US008952178B2

(12) United States Patent
Zhang et al.

(10) Patent No.: US 8,952,178 B2
(45) Date of Patent: Feb. 10, 2015

(54) THIOPHENE DERIVATIVES

(75) Inventors: Hesheng Zhang, Tianjin (CN); Guanghuai Zeng, Tianjin (CN); Yifei Gao, Tianjin (CN)

(73) Assignees: Tianjin Hemay Bio-Tech Co., Ltd., Tianjin (CN); Tianjin Michele Sci-Tech Development Co., Ltd., Tianjin (CN)

( * ) Notice: Subject to any disclaimer, the term of this patent is extended or adjusted under 35 U.S.C. 154(b) by 0 days.

(21) Appl. No.: 13/320,533

(22) PCT Filed: May 14, 2010

(86) PCT No.: PCT/CN2010/072767
§ 371 (c)(1),
(2), (4) Date: Jan. 10, 2012

(87) PCT Pub. No.: WO2010/130224
PCT Pub. Date: Nov. 18, 2010

(65) Prior Publication Data
US 2012/0107269 A1 May 3, 2012

(30) Foreign Application Priority Data
May 14, 2009 (CN) .......................... 2009 1 0068831

(51) Int. Cl.
A61K 31/381 (2006.01)
C07D 495/04 (2006.01)
A61K 31/407 (2006.01)
A61K 45/06 (2006.01)

(52) U.S. Cl.
CPC ............ *C07D 495/04* (2013.01); *A61K 31/407* (2013.01); *A61K 45/06* (2013.01)
USPC .......................................... 548/453; 514/421

(58) Field of Classification Search
USPC .................................. 548/453; 514/412, 421
See application file for complete search history.

(56) References Cited

U.S. PATENT DOCUMENTS

| | | | |
|---|---|---|---|
| 6,020,358 A | 2/2000 | Muller et al. | |
| 6,962,940 B2 | 11/2005 | Muller et al. | |
| 7,208,516 B2 | 4/2007 | Muller et al. | |
| 7,427,638 B2 | 9/2008 | Muller et al. | |
| 7,659,302 B2 | 2/2010 | Muller et al. | |
| 7,893,101 B2 | 2/2011 | Muller et al. | |
| 8,455,536 B2 | 6/2013 | Muller et al. | |
| 2004/0091454 A1 | 5/2004 | Zeldis | |
| 2006/0183787 A1 | 8/2006 | Muller et al. | |
| 2006/0183788 A1 | 8/2006 | Muller et al. | |
| 2007/0155791 A1 | 7/2007 | Zeldis et al. | |
| 2007/0207121 A1 | 9/2007 | Zeldis | |
| 2008/0051432 A1 | 2/2008 | Zhang | |
| 2008/0176900 A1 | 7/2008 | Zhang | |
| 2008/0234359 A1 | 9/2008 | Muller et al. | |
| 2008/0269123 A1 | 10/2008 | Li et al. | |

FOREIGN PATENT DOCUMENTS

| | | | |
|---|---|---|---|
| AU | 2006200033 A1 | | 2/2006 |
| CN | 1420889 A | | 5/2003 |
| CN | 101186612 | * | 5/2008 |
| CN | 101186612 A | | 5/2008 |
| WO | WO-00/25777 | * | 5/2000 |
| WO | WO 00/25777 | | 5/2000 |
| WO | WO 01/34606 A1 | | 5/2001 |
| WO | 03/080048 A1 | | 10/2003 |
| WO | 03/080049 A1 | | 10/2003 |
| WO | 2005/115465 A1 | | 12/2005 |
| WO | 2006/065814 A1 | | 6/2006 |
| WO | 2006/128675 A1 | | 12/2006 |
| WO | 2007/042035 A2 | | 4/2007 |
| WO | 2007/139150 A1 | | 12/2007 |
| WO | 2008/095720 A1 | | 8/2008 |
| WO | 2009/002746 A1 | | 12/2008 |
| WO | 2009/011893 A2 | | 1/2009 |
| WO | 2009/011897 A1 | | 1/2009 |
| WO | 2009/013286 A1 | | 1/2009 |
| WO | 2009/045397 A1 | | 4/2009 |

(Continued)

OTHER PUBLICATIONS

International Search Report dated Aug. 26, 2010, issued in related International Patent Appln. No. PCT/CN2010/072767, filed May 14, 2010.
Man, Hon-Wah et al., "Discovery of (S)-N-[2-[1-(3-ethoxy-4-methoxyphenyl)-2-methanesulfonylethyl]-1,3-dioxo-2,3-dihydro-1H-isoindol-4-yl] acetamide (apremilast), a potent and orally active phosphodiesterase 4 and tumor necrosis factor-alpha inhibitor," Mar. 3, 2009, J. Med. Chem., vol. 52, No. 6, pp. 1522-1524.
Banner, Katharine H. and Trevethick, Michael A., "PDE4 inhibition: a novel approach for the treatment of inflammatory bowel disease," *TRENDS in Pharmacological Sciences*, 25(8):430-436 (2004).
Bäumer, Wolfgang et al., "Highly Selective Phosphodiesterase 4 Inhibitors for the Treatment of Allergic Skin Diseases and Psoriasis," *Inflammation & Allergy—Drug Targets*, 6:17-26 (2006).

(Continued)

*Primary Examiner* — Yong Chu
*Assistant Examiner* — Sonya Wright
(74) *Attorney, Agent, or Firm* — Kilpatrick Townsend & Stockton LLP

(57) ABSTRACT

Disclosed is a compound of formula (I),

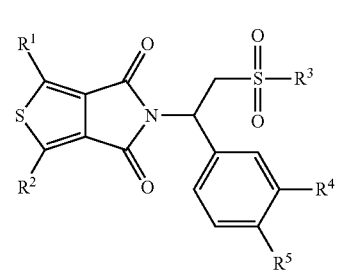

formula (I)

wherein
$R^1$, $R^2$, $R^3$, $R^4$, $R^5$, $R^6$, $R^7$ and $R^8$ are as defined in the present application.

22 Claims, No Drawings

(56) References Cited

FOREIGN PATENT DOCUMENTS

| WO | 2009/120167 A1 | 10/2009 |
|---|---|---|
| WO | 2009/151569 A2 | 12/2009 |

OTHER PUBLICATIONS

Castro, Ana et al., "Cyclic Nucleotide Phosphodiesterases and Their Role in Immunomodulatory Responses: Advances in the Development of Specific Phosphodiesterase Inhibitors," *Medicinal Research Reviews*, 25(2):229-244 (2005).

Chen, Thomas C. et al., "The Type IV Phosphodiesterase Inhibitor Rolipram Induces Expression of the Cell Cycle Inhibitors $P21^{Clip1}$ And $P27^{Kip1}$, Resulting in Growth Inhibition, Increased Differentiation, and Subsequent Apoptosis of Malignant A-172 Glioma Cells," *Cancer Biology & Therapy* 1(3):268-276 (2002).

Erdogan, Suat et al., "The effects of increased cAMP content on inflammation, oxidative stress and PDE4 transcripts during *Brucella melitensis* infection," *Research in Veterinary Science*, 84:18-25 (2008).

Jeffery, Peter, "Phosphodiesterase 4-selective inhibition: novel therapy for the inflammation of COPD," *Pulmonary Pharmacology & Therapeutics*, 18:9-17 (2005).

Kasugai, Shohei and Miyamoto, Ken-ichi, "Potential of PDE4 Inhibitors in the Treatment of Osteopenia," *Drug News Perspect*, 12(9):529-534, (1999).

Lerner, Adam et al., "The cAMP Signaling Pathway as a Therapeutic Target in Lymphoid Malignancies," *Leukemia and Lymphoma*, 37(1-2):39-51 (2000).

Link, Andreas et al., "Phosphodiesterase 4 inhibition but no beta-adrenergic stimulation suppresses tumor necrosis factor-alpha release in peripheral blood mononuclear cells in septic shock," *Critical Care*, 12(6):R159 (2008).

Lipworth, Brian J, "Phosphodiesterase-4 inhibitors for asthma and chronic obstructive pulmonary disease," *Lancet* 365:167-75 (2005).

Liu, Susana et al., "Dynamic Activation of Cystic Fibrosis Transmembrane Conductance Regulator by Type 3 and Type 4D Phosphodiesterase Inhibitors," *The Journal of Pharmacology and Experimental Therapeutics*, 314:846-854 (2005).

Marfat, A et al., "Nicotinamide Derivatives as Selective Inhibitors of PDE4," *Exp. Opin. Ther. Patents*, 9(4):481-485 (1999).

Marquette, Amélie et al., "ERK and PDE4 cooperate to induce RAF isoform switching in melanoma," *Nature Structural & Molecular Biology*, 18(5):584-592 (2011).

Monneaux, Fanny and Muller, Sylviane, "Molecular therapies for systemic lupus erythematosus: clinical trials and future prospects," *Arthritis Research & Therapy*, 11(3):234 (2009).

Nadal, D et al., "Tumour necrosis factor-α in infectious meningitis," *Archives of Disease in Childhood*, 64:1274-1279 (1989).

Narita, Motoshi et al., Phosphodiesterase 4 in osteoblastic osteosarcoma cells as a potential target for growth inhibition, *Anti-Cancer Drugs*, 14:377-381 (2003).

Ogawa, Ryosuke et al., "Inhibition of PDE4 phosphodiesterase activity induces growth suppression, apoptosis, glucocorticoid sensitivity, p53, and $p21^{WAF1/CIP1}$ proteins in human acute lymphoblastic leukemia cells," *Blood*, 99(9):3390-3397 (2002).

Savai, Rajkumar et al., "Targeting cancer with phosphodiesterase inhibitors," *Expert Opinion on Investigational Drugs*, 19:117-131 (2010).

Secchiero, Paola et al., "Pivotal role of cyclic nucleoside phosphodiesterase 4 in Tat-mediated $CD4^+$ T cell hyperactivation and HIV type 1 replication," *PNAS*, 97(26):14620-14625 (2000).

Sengupta, Rajarshi et al., "Treating brain tumors with PDE4 inhibitors," *Trends in Pharmacological Sciences*, 32(6):337-344 (2011).

Shenoy, Padmanabha et al., "Phosphodiesterase inhibitors in the management of autoimmune disease," *Autoimmunity Reviews*, 9:511-515 (2010).

Soares, A C et al., "Impaired host defense to *Klebsiella pneumoniae* infection in mice treated with the PDE4 inhibitor rolipram," *British Journal of Pharmacology*, 140: 855-862 (2003).

Sommer N, et al., "Therapeutic potential of phosphodiesterase type 4 inhibition in chronic autoimmune demyelinating disease," *Journal of Neuroimmunology*, 79(1):54-61 (1997).

Souza, Danielle G. et al., "Effects of inhibition of PDE4 and TNF-α on local and remote injuries following ischaemia and reperfusion injury," *British Journal of Pharmacology*, 134:985-994 (2001).

Taguchi, I. et al., "Protection by a cyclic AMP-specific phosphodiesterase inhibitor, rolipram, and dibutyryl cyclic AMP against Propionibacterium acnes and lipopolysaccharide-induced mouse hepatitis," *Inflamm Res Off J Eur Histamine Res Soc.*, 48(7):380-5 (1999).

Wang, Yanping et al., "Sanjay M. Mallya, Matthew O. Sikpi. Calmodulin antagonists and cAMP inhibit ionizing-radiation-enhancement of double-strand-break repair in human cells," *Mutation Research/DNA Repair*, 460:29-39 (2000).

Weber, Michael et al., "Mechanisms of Cyclic Nucleotide Phosphodiesterases in Modulating T Cell Responses in Murine Graft-versus-Host Disease," *PLoS ONE*, 8(3):1-10 (2013).

Woyda, K. et al., "Inhibition of phosphodiesterase 4 enhances lung alveolarisation in neonatal mice exposed to hyperoxia," *European Respiratory Journal*, 33: 861-870 (2009).

Giembycz, "Can the anti-inflammatory potential of PDE4 inhibitors be realized: guarded optimism or wishful thinking?", *British Journal of Pharmacology*, vol. 155, pp. 288-290 (2008).

Gottlieb et al., "An open-label, single-arm pilot study in patients with severe plaque-tye psoriasis treated with an oral anti-inflammatory agent, apremilast", *Current medical Research and Opinion*, vol. 24, No. 5, pp. 1529-1538 (2008).

Khobzaoui et al., "CC-10004 Celgene", *Current Opinion in Investigational Drugs*, vol. 6, No. 5, pp. 518-525 (2005).

Molostvov et al., "The effects of selective cytokine inhibitory drugs (CC-10004 and CC-1088) on VEGF and IL-6 expression and apoptosis in myeloma and endothelial cell co-cultures", *British Journal of Haematology*, vol. 124, pp. 366-375 (2004).

Schafer et al., "Apremilast, a cAMP phosphodiesterase-4 inhibitor, demonstrates anti-inflammatory activity in vitro and in a model of psoriasisbph", *British Journal of Pharmacology*, vol. 159, pp. 842-855 (2010).

Baumer et al., "Highly Selective Phosphodiesterase 4 Inhibitors for the Treatment of Allergic Skin Diseases and Psoriasis", *Inflammation & Allergy—Drug Targets*, vol. 6, pp. 17-26 (2006).

Man et al., "Discovery of (S)-N-{2-[1-(3-Ethoxy-4-methoxyphenyl)-2-methanesulfonylethyl]-1,3-dioxo-2,3-dihydro-1H-isoindol-4-yl}acetamide (Apremilast), a Potent and Orally Active Phosphodiesterase 4 and Tumor Necrosis Factor-α Inhibitor", *J. Med. Chem.*, vol. 52, p. 1522-1524 (2009).

\* cited by examiner

THIOPHENE DERIVATIVES

CROSS-REFERENCE TO RELATED APPLICATIONS

The present application is the U.S. National Phase entry under 35 U.S.C. §371 and claims the benefit of International Application No. PCT/CN2010/072767, filed May 14, 2010, which claims the benefit of Chinese Patent Application No. 200910068831.1, filed on May 14, 2009, the contents of which are incorporated by reference for all purposes.

FIELD

The present application relates to the field of organic chemistry and pharmaceutical chemistry.

BACKGROUND

TNFα is a cytokine mainly released by mononuclear phagocytes when responding to immunostimulants. TNFα is capable of facilitating most of the processes, such as differentiation, aggregation and proliferation of cells, degradation of protein, and the like. TNFα has protective effects on prevention of infectious substances, tumors and tissue damages at a low level. However, excessive release of TNFα will induce diseases. For example, when TNFα is administered to mammals or humans, it will induce or aggravate inflammation, fever, cardiovascular effects, bleeding, clotting and acute response similar to acute infection and shock conditions. The excess or uncontrolled amount of TNFα produced in bodies of animals or humans often indicates suffering from the following diseases: endotoxemia and/or toxic shock syndromes, cachexia, adult respiratory nervous syndromes, cancers (such as solid tumors and haemal tumors), heart diseases (such as congestive heart failure), virus infections, genetic diseases, inflammatory diseases, allergic diseases or autoimmune diseases.

Cancer is a particularly destructive disease. The increased level of TNFα in blood indicates risks for suffering from cancers or diffusion of cancers. Generally, cancerous cells cannot survive in the circulating system of a healthy subject. One reason lies in that the interior wall of a vessel is a barrier for oncocyte extravasating. Studies demonstrate that the ELAM-1 on endothelial cells can mediate the facilitation of colon cancer cells to adhere to endothelium treated with cytokines.

Cyclic adenosine monophosphate (cAMP) also acts in many diseases and disorders, such as, but not limited to, asthma, inflammation and other disorders. The increased concentration of cAMP in leucocytes, when inflammation occurs, will inhibit the activation of leucocytes, and then release inflammation regulatory factors including TNFα, NF-κB and the like. The increased level of cAMP will also cause chalasis of airway smooth muscle.

The main cellular mechanism of the inactivation of cAMP is a family of isoenzymes known as cyclic nucleotide phosphodiesterase (PDE) destroys cAMP. It is known there are eleven members in the PDE family. Up to now, it has been demonstrated that the inhibition of PDE4 enzyme is particularly effective on inhibiting the release of inflammation mediators and the chalasis of airway smooth muscle. Therefore, PDE4 enzyme has been one of the drug targets of interest. The inhibition of PDE4 enzyme causes the increased level of cAMP, and thus regulates the level of TNFα to achieve the treatment of inflammation, such as septic shock, ichorrhemia, endotoxin shock, hemic shock, septic disease syndrome, ischemia reperfusion injury, mycobacterium malaria infection, meningitis, psoriasis, congestive heart failure, fibrotic disease, cachexia, graft rejection, tumor, autoimmune disorder disease, AIDS opportunity infection, rheumatic arthritis, rheumatoidspondylitis, osteoarthritis, other inflammatory disease, Crohn's disease, ulcerative colitis, multiple sclerosis, systemic lupus erythematosus, erythema nodosum leprosum, radiation damage, hyperoxic lung injury and the like, infective disease, immune disease or other malignant disease.

Current PDE4 enzyme inhibitors exhibit clinical effectiveness on several inflammatory diseases including asthma, chronic obstructive pulmonary disease (COPD), allergic rhinitis, allergic dermatitis and the like. In animal models they also show effectiveness on various other diseases including arthritis, ichorrhemia and the like. However, they have adverse reactions, such as nausea, vomiting, and the like because they cannot specifically inhibit PDE4 enzyme such that the clinical practice thereof has been limited. Therefore, specific PDE4 enzyme inhibitors are possible to reduce the adverse reactions of a drug and maintain their anti-inflammatory activity.

SUMMARY

In one aspect, the present application relates to a compound of formula (I), a stereoisomer, an enantiomer or a tautomer thereof, or a mixture of stereoisomers thereof, a pharmaceutically acceptable salt thereof, a polymorph thereof, a solvate thereof, a prodrug thereof or a metabolite thereof:

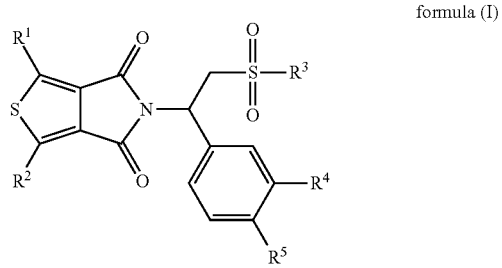

formula (I)

wherein, $R^1$ and $R^2$ are each independently selected from the group consisting of hydrogen, halogen, optionally substituted alkyl, optionally substituted alkoxy, hydroxy, cyano, nitro and optionally substituted $NR^6R^7$;

$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;

$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;

$R^6$ and $R^7$ are each independently selected from the group consisting of hydrogen, optionally substituted alkyl, optionally substituted aryl, optionally substituted $C(O)R^8$ and optionally substituted $SO_2R^8$, or $R^6$ and $R^7$ together represent optionally substituted 1,4-butylidene, optionally substituted 1,5-pentylidene, optionally substituted 1,6-hexylidene or optionally substituted CH$_2$CH$_2$XCH$_2$CH$_2$, wherein X is selected from the group consisting of O, S and NR$^8$; and R$^8$ is selected from the group consisting of hydrogen and optionally substituted alkyl.

In another aspect, the present application relates to a process for preparing a compound of formula (I), comprising reacting a compound of formula (A-IV) with a compound of formula (A-VII) to obtain the compound of formula (I):

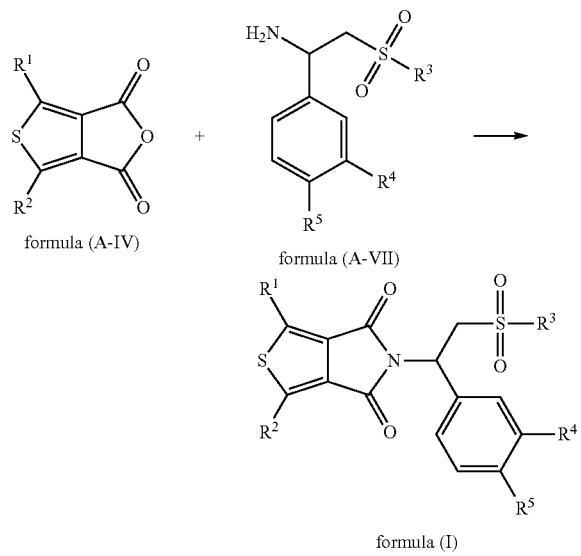

formula (A-IV)

formula (A-VII)

formula (I)

wherein,

R$^1$ and R$^2$ are each independently selected from the group consisting of hydrogen, halogen, optionally substituted alkyl, optionally substituted alkoxy, hydroxy, cyano, nitro and optionally substituted NR$^6$R$^7$;

R$^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted NR$^6$R$^7$;

R$^4$ and R$^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;

R$^6$ and R$^7$ are each independently selected from the group consisting of hydrogen, optionally substituted alkyl, optionally substituted aryl, optionally substituted C(O)R$^8$ and optionally substituted SO$_2$R$^8$, or R$^6$ and R$^7$ together represent optionally substituted 1,4-butylidene, optionally substituted 1,5-pentylidene, optionally substituted 1,6-hexylidene or optionally substituted CH$_2$CH$_2$XCH$_2$CH$_2$, wherein X is selected from the group consisting of O, S and NR$^8$;

R$^8$ is selected from the group consisting of hydrogen and optionally substituted alkyl.

In still another aspect, the present application relates to a pharmaceutical composition comprising a pharmaceutically acceptable carrier and a therapeutically effective amount of a compound of formula (I), a stereoisomer, an enantiomer or a tautomer thereof, or a mixture of stereoisomers thereof, a pharmaceutically acceptable salt thereof, a polymorph thereof, a solvate thereof, a prodrug thereof or a metabolite thereof,

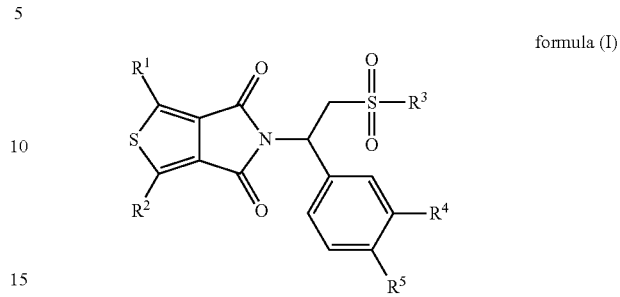

formula (I)

wherein,

R$^1$ and R$^2$ are each independently selected from the group consisting of hydrogen, halogen, optionally substituted alkyl, optionally substituted alkoxy, hydroxy, cyano, nitro and optionally substituted NR$^6$R$^7$;

R$^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted NR$^6$R$^7$;

R$^4$ and R$^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;

R$^6$ and R$^7$ are each independently selected from the group consisting of hydrogen, optionally substituted alkyl, optionally substituted aryl, optionally substituted C(O)R$^8$ and optionally substituted SO$_2$R$^8$, or R$^6$ and R$^7$ together represent optionally substituted 1,4-butylidene, optionally substituted 1,5-pentylidene, optionally substituted 1,6-hexylidene or optionally substituted CH$_2$CH$_2$XCH$_2$CH$_2$, wherein X is selected from the group consisting of O, S and NR$^8$;

R$^8$ is selected from the group consisting of hydrogen and optionally substituted alkyl.

In yet another aspect, the present application relates to a method for reducing activity of PDE4 enzyme, comprising contacting PDE4 enzyme with a therapeutically effective amount of a compound of formula (I), a stereoisomer, an enantiomer or a tautomer thereof, or a mixture of stereoisomers thereof, a pharmaceutically acceptable salt thereof, a polymorph thereof, a solvate thereof, a prodrug thereof or a metabolite thereof,

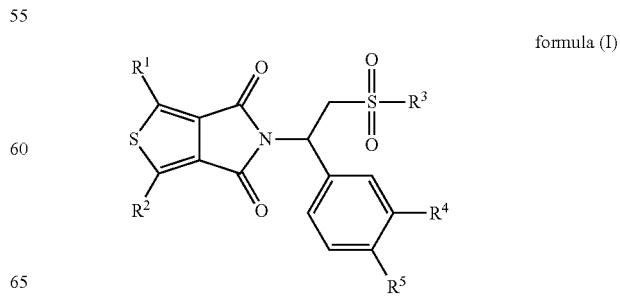

formula (I)

wherein,

R$^1$ and R$^2$ are each independently selected from the group consisting of hydrogen, halogen, optionally substituted alkyl, optionally substituted alkoxy, hydroxy, cyano, nitro and optionally substituted NR$^6$R$^7$;

R$^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted NR$^6$R$^7$;

R$^4$ and R$^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;

R$^6$ and R$^7$ are each independently selected from the group consisting of hydrogen, optionally substituted alkyl, optionally substituted aryl, optionally substituted C(O)R$^8$ and optionally substituted SO$_2$R$^8$, or R$^6$ and R$^7$ together represent optionally substituted 1,4-butylidene, optionally substituted 1,5-pentylidene, optionally substituted 1,6-hexylidene or optionally substituted CH$_2$CH$_2$XCH$_2$CH$_2$, wherein X is selected from the group consisting of O, S and NR$^8$;

R$^8$ is selected from the group consisting of hydrogen and optionally substituted alkyl.

In still another aspect, the present application relates to a method for treating diseases or conditions mediated by PDE4 enzyme, comprising administering to a subject in need thereof a therapeutically effective amount of a compound of formula (I), a stereoisomer, an enantiomer or a tautomer thereof, or a mixture of stereoisomers thereof, a pharmaceutically acceptable salt thereof, a polymorph thereof, a solvate thereof, a prodrug thereof or a metabolite thereof,

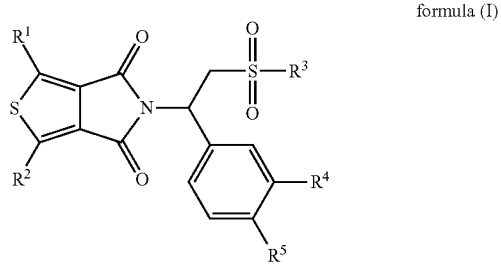

formula (I)

wherein,

R$^1$ and R$^2$ are each independently selected from the group consisting of hydrogen, halogen, optionally substituted alkyl, optionally substituted alkoxy, hydroxy, cyano, nitro and optionally substituted NR$^6$R$^7$;

R$^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted NR$^6$R$^7$;

R$^4$ and R$^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;

R$^6$ and R$^7$ are each independently selected from the group consisting of hydrogen, optionally substituted alkyl, optionally substituted aryl, optionally substituted C(O)R$^8$ and optionally substituted SO$_2$R$^8$, or R$^6$ and R$^7$ together represent optionally substituted 1,4-butylidene, optionally substituted 1,5-pentylidene, optionally substituted 1,6-hexylidene or optionally substituted CH$_2$CH$_2$XCH$_2$CH$_2$, wherein X is selected from the group consisting of O, S and NR$^8$;

R$^8$ is selected from the group consisting of hydrogen and optionally substituted alkyl.

DETAIL DESCRIPTION

In the following description, certain specific details are included to provide a thorough understanding for various disclosed embodiments. One skilled in the relevant art, however, will recognize that the embodiments may be practiced without one or more these specific details, or with other methods, components, materials, etc.

Unless the context required otherwise, throughout the specification and claims which follows, the term "comprise" and variations thereof, such as "comprises" and "comprising" are to be construed in an open, inclusive sense, which is as "include, but not limited to".

Reference throughout this specification to "one embodiment", or "an embodiment", or "in another embodiment", or "in some embodiments" means that a particular referent feature, structure or characteristic described in connection with the embodiments is included in at least one embodiment. Therefore, the appearance of the phrases "in one embodiment", or "in the embodiment", or "in another embodiment", or "in some embodiments" in various places throughout this specification are not necessarily all referring to the same embodiment. Moreover, the particular features, structures or characteristics may be combined in any suitable manner in one or more embodiments.

It should be noted that, as used in this specification and the appended claims, the singular forms "a", "an" and "the" include plural referents unless the context clearly stated otherwise. Therefore, for example, a reaction comprising "a catalyst" comprises one catalyst, two or more catalysts. It should be also noted that the use of "or" means "and/or" unless stated otherwise.

Definitions

Certain chemical groups named herein are preceded by a shorthand notation indicating the total number of carbon atoms that are to be found in the indicated chemical group. For example, C$_7$-C$_{12}$ alkyl describes an alkyl, as defined below, having a total of 7 to 12 carbon atoms, and C$_4$-C$_{12}$ cycloalkylalkyl describes a cycloalkylalkyl, as defined below, having a total of 4 to 12 carbon atoms. The total number of carbon atoms in the shorthand notation does not include carbons that may exist in substituents of the groups described.

Accordingly, as used in the specification and appended claims, unless specified to the contrary, the following teens have the meanings indicated:

"Hydroxy" refers to the —OH group.

"Cyano" refers to the —CN group.

"Nitro" refers to the —NO$_2$ group.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a straight or branched hydrocarbon chain group consisting of from two to eight carbon atoms and at least one carbon-carbon double bond, which is attached to the rest of the molecule by a single bond, e.g., ethenyl, prop-1-enyl, but-1-enyl, pent-1-enyl, pent-1,4-dienyl, and the like. An "alkyne" moiety refers to a straight or branched hydrocarbon chain group consisting of from two to eight carbon atoms and at least one carbon-carbon triple bond, which is attached to the rest of the molecule by a single bond. The alkyl moiety, whether saturated or unsaturated, may be branched chain or straight chain.

The alkyl group may have 1 to 20 carbon atoms (whenever it appears herein, a numerical range such as "1 to 20" refers to each integer in the given number range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of term "alkyl" where no numerical range is designated). The alkyl group may also be a medium size alkyl having 1 to 10 carbon atoms. The alkyl group may also be a lower alkyl having 1 to 5 carbon atoms. The alkyl group of compounds of the present application may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl.

The alkyl group may be optionally substituted, i.e., substituted or unsubstituted. When substituted, the substituted group(s) is(are) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyanato, isothiocyanato, nitro, silyl, trihalomethanesulfonyl, —NR'R" or amino including mono- and di-substituted amino group, and the protected derivatives thereof. Typical alkyl groups include, but are in no way limited to, methyl, ethyl, propyl, isopropyl, butyl, isobutyl, t-butyl, pentyl, hexyl, ethyl, propenyl, butenyl, cyclopropyl, cyclobutyl, cyclopentyl, cyclohexyl, and the like. Whenever a substituent is described as being "optionally substituted", that substituent may be substituted with one of the above substituents.

"$C_1$-$C_4$ alkyl" refers to an alkyl group as defined above containing one to four carbon atoms. The $C_1$-$C_4$ alkyl group may be optionally substituted as defined for an alkyl group.

"$C_1$-$C_6$ alkyl" refers to an alkyl group as defined above containing one to six carbon atoms. The $C_1$-$C_6$ alkyl group may be optionally substituted as defined for an alkyl group.

"$C_1$-$C_{12}$ alkyl" refers to an alkyl group as defined above containing one to twelve carbon atoms. The $C_1$-$C_{12}$ alkyl group may be optionally substituted as defined for an alkyl group.

"$C_2$-$C_6$ alkyl" refers to an alkyl group as defined above containing two to six carbon atoms. The $C_2$-$C_6$ alkyl group may be optionally substituted as defined for an alkyl group.

"$C_3$-$C_6$ alkyl" refers to an alkyl group as defined above containing three to six carbon atoms. The $C_3$-$C_6$ alkyl group may be optionally substituted as defined for an alkyl group.

"$C_3$-$C_{12}$ alkyl" refers to an alkyl group as defined above containing three to twelve carbon atoms. The $C_3$-$C_{12}$ alkyl group may be optionally substituted as defined for an alkyl group.

"$C_6$-$C_{12}$ alkyl" refers to an alkyl group as defined above containing six to twelve carbon atoms. The $C_6$-$C_{12}$ alkyl group may be optionally substituted as defined for an alkyl group.

"$C_7$-$C_{12}$ alkyl" refers to an alkyl group as defined above containing seven to twelve carbon atoms. The $C_7$-$C_{12}$ alkyl group may be optionally substituted as defined for an alkyl group.

As used herein, "alkoxy" refers to the formula —OR, wherein R is an alkyl group defined as above, e.g., methoxy, ethoxy, n-propoxy, 1-methyl ethoxy (isopropoxy), n-butoxy, iso-butoxy, sec-butoxy, t-butoxy, amoxy, t-amoxy, and the like. As used herein, "alkylthio" refers to the formula —SR, wherein R is an alkyl group defined as above, e.g., methylmercapto, ethylmercapto, n-propylmercapto, 1-methylethylmercapto (iso-propylmercapto), n-butylmercapto, iso-butylmercapto, sec-butylmercapto, t-butylmercapto, and the like.

As used herein, "alkylene" refers to a straight or branched divalent hydrocarbon chain linking the rest of the molecule to a radical group, consisting of carbon and hydrogen and having from one to eight carbon atoms, e.g., methylene, ethylene, propylene, n-butylene, ethenylene, propenylidene, n-butenylidene. The alkylene chain may be attached to the rest of the molecule and to the radical group through one carbon within the chain or through any two carbons within the chain.

As used herein, "aryl" refers to a carbocyclic (all carbon) ring or two or more fused rings (rings that share two adjacent carbon atoms) that have a fully delocalized pi-electron system. Examples of an aryl group include, but are not limited to, fluorenyl, phenyl and naphthyl. The aryl group, e.g., may contain five to twelve carbon atoms. An aryl group of the present application may be substituted or unsubstituted. When substituted, the hydrogen atoms are replaced by substituent group(s) that is(are) one or more group(s) independently selected from alkyl, cycloalkyl, aryl, heteroaryl, heteroalicyclyl, hydroxy, protected hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, protected C-carboxyl, O-carboxyl, isocyanato, thiocyanato, isothiocyanato, nitro, silyl, trihalomethanesulfonyl, —NR'R" (R' and R" are alkyl groups as defined in the present application) or protected amino.

As used herein, the term "halo" refers to bromo, chloro, fluoro or iodo.

"Cycloalkyl" refers to a non-aromatic monocyclic or bicyclic hydrocarbon group consisting solely of carbon and hydrogen atoms, having from three to fifteen carbon atoms, preferably having from three to twelve carbon atoms, and which is saturated or unsaturated stable and attached to the rest of the molecule by a single bond, e.g., cyclopropyl, cyclobutyl, cyclopentyl, cyclohexyl, cyclodecyl and the like. Unless otherwise stated specifically in the specification, the term "cycloalkyl" is meant to include cycloalkyl groups which are optionally substituted by one or more substituents selected from the group consisting of cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyanato, isothiocyanato, nitro, silyl, trihalomethanesulfonyl, —NR'R" (R' and R" are alkyl groups as defined in the present application) or amino including mono-substituted and di-substituted amino group, and the protected derivatives thereof.

"$C_3$-$C_6$ cycloalkyl" refers to a cycloalkyl group as defined above containing three to six carbon atoms. The $C_3$-$C_6$ cycloalkyl group may be optionally substituted as defined for a cycloalkyl.

"$C_3$-$C_{10}$ cycloalkyl" refers to a cycloalkyl group as defined above containing three to ten carbon atoms. The $C_3$-$C_{10}$ cycloalkyl group may be optionally substituted as defined for a cycloalkyl.

"$C_3$-$C_{12}$ cycloalkyl" refers to a cycloalkyl group as defined above containing three to twelve carbon atoms. The $C_3$-$C_{12}$ cycloalkyl group may be optionally substituted as defined for a cycloalkyl.

As used herein, "heterocyclyl" refers to a stable 3- to 12-membered non-aromatic ring group which consists of carbon atoms and from one to five heteroatoms selected from the group consisting of nitrogen, oxygen and sulphur. Examples of such heterocyclyl groups include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. Unless stated otherwise specifically in the specification, the term "heterocycloalkyl" is meant to include heterocyclyl groups as defined above which are optionally substituted by one or more substituents selected from the group consisting of cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyanato, isothiocyanato, nitro, silyl, trihalomethanesulfonyl, —NR'R" (R' and R" are alkyl groups as defined in the present application) or amino including mono-substituted and di-substituted amino group, and the protected derivatives thereof.

"Prodrugs" is meant to indicate a compound that may be converted under physiological conditions or by solvolysis to a biologically active compound of the present application. Therefore, the term "prodrug" refers to a metabolic precursor of a compound of the present application that is pharmaceutically acceptable. A prodrug may be inactive when administered to a subject in need thereof, but is converted in vivo to an active compound of the present application. Prodrugs are typically rapidly transformed in vivo to yield the parent compound of the present application, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al, "Pro-drugs as Novel Delivery Systems" A.C.S. Symposium Series, Vol. 14 and in Bioreversible Carriers in Drug Design, ed. Edward B. Roche, American Pharmaceutical Association and Pergamon Press, 1987, both of which are incorporated in full by reference herein.

The term "prodrug" is also meant to include any convalently bonded carriers which release the active compound of the present application in vivo when such prodrug is administered to a mammalian subject. Prodrugs of a compound of the present application may be prepared by modifying functional groups present in the compound of the present application in such a way that the modifications are cleaved, either in routine manipulation or in vivo, to the parent compound of the present application. Prodrugs include compounds of the present application wherein a hydroxy, amino or mercapto group is bonded to any groups that, when the prodrug of the compound of the present application is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the present application and the like.

"Optional" or "optionally" means that the subsequently described event of circumstances may or may not occur, and that the description includes instances where said event or circumstance occurs and instances in which it does not. For example, "optionally substituted aryl" means that the aryl group may or may not be substituted and the description includes both substituted aryl groups and aryl groups having no substitution.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effects on preparing a pharmaceutical composition.

"Pharmaceutically acceptable salts" include both "pharmaceutically acceptable acid addition salts" and "pharmaceutically acceptable base addition salts".

"Pharmaceutically acceptable acid addition salt" refers to those salts whichi retain the biological effectiveness and properties of the free bases, which are not biologically or otherwise undesirable, and which re formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic or an organic base to the free acid. Salts derived from inorganic bases include, but are not limited, to sodium, potassium, lithium, ammonium, calcium, magnesium, iron, zinc, copper, manganese, aluminium salts and the like. Preferred inorganic salts are the ammonium, sodium, potassium, calcium, and magnesium salts. Salts derived from organic bases include, but are not limited t, salts of primary, secondary and tertiary amines, substituted amines including naturally occurring substituted amines, cyclic amines and s basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucosamine, theobromine, triethanolamine, trometamol, purine, piperazine, piperidine, N-ethyl piperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the present application. As used herein, the term "solvate" refers to an aggregate that comprises one or more molecules of a compound of the present application with one or more molecules of solvent. The solvent may be water, in which case the solvate may be a hydrate. Alternatively, the solvent may be an organic solvent. Therefore, the compounds of the present application may exist as a hydrate, including monohydrate, dihydrate, hemihydrate, sesquihydrate, trihydrate, tetrahydrate and the like, as well as the corresponding solvated forms. The compound of the present application may be true solvate, while in other cases, the compound of the present application may merely retain adventitious water or be a mixture of water plus some adventitious solvent.

The "polymorph" refers to a component having an identical chemical formula but having different structures.

A "pharmaceutical composition" refers to a formulation of a compound of the present application and a medium generally acceptable in the art for the delivery of the biologically active compound to mammals, e.g., humans. Such a medium includes all pharmaceutically acceptable carriers, diluents or excipients therefor.

"Therapeutically effective amount" refers to that amount of a compound of the present application which, when administered to a mammal, preferably a human, is sufficient to effect treatment, as defined below, of an PDE4 enzyme mediated disease or condition in the mammal, preferably a human. The amount of a compound of the present application which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the present application or their pharmaceutically acceptable salt may contain one or more asymmetric centers and may thus give rise to enantiomers, diastereoisomers, and other stereoismeric forms that may be defined, in terms of absolute stereochemistry, as (R)- or (S)-, or (D)- or (L)- for amino acids. The present application is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present application contemplates various stereoisomers and mixtures thereof.

A "tautomer" refers to a proton shift from one atom of a molecule to another atom of the same molecule. The present application includes tautomers of any said compound.

Specific Embodiments

In one aspect, the present application relates to a compound of formula (I), a stereoisomer, an enantiomer or a tautomer, or a mixture of stereoisomers thereof, a pharmaceutically acceptable salt thereof, a polymorph thereof, a solvate thereof, a prodrug thereof or a metabolite thereof:

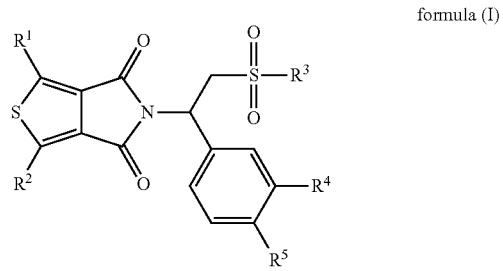

formula (I)

wherein, $R^1$ and $R^2$ are each independently selected from the group consisting of hydrogen, halogen, optionally substituted alkyl, optionally substituted alkoxy, hydroxy, cyano, nitro and optionally substituted $NR^6R^7$;

$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;

$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;

$R^6$ and $R^7$ are each independently selected from the group consisting of hydrogen, optionally substituted alkyl, optionally substituted aryl, optionally substituted $C(O)R^8$ and optionally substituted $SO_2R^8$, or $R^6$ and $R^7$ together represent optionally substituted 1,4-butylidene, optionally substituted 1,5-pentylidene, optionally substituted 1,6-hexylidene or optionally substituted CH₂CH₂XCH₂CH₂, wherein X is selected from the group consisting of O, S and NR⁸;

R⁸ is selected from the group consisting of hydrogen and optionally substituted alkyl.

In some embodiments, $C_1$-$C_8$ alkyl is selected from the group consisting of $C_1$-$C_4$ alkyl and $C_1$-$C_6$ alkyl.

In some embodiments, $C_1$-$C_8$ alkoxy is selected from the group consisting of $C_1$-$C_4$ alkoxy and $C_1$-$C_6$ alkoxy.

In some embodiments, $C_1$-$C_8$ alkylthio is selected from the group consisting of $C_1$-$C_4$ alkylthio and $C_1$-$C_6$ alkylthio.

In some embodiments, $C_3$-$C_{10}$ cycloalkyl is selected from $C_3$-$C_6$ cycloalkyl.

In some embodiments, $R^1$ and $R^2$ are each independently selected from the group consisting of hydrogen, methyl, ethyl, nitro, NH₂, NHCH₃, CH₃C(O)NH, CH₃CH₂C(O)NH, CH₃SO₂NH and ClCH₂C(O)NH.

In some embodiments, $R^3$ is selected from the group consisting of $C_1$-$C_8$ alkyl and $C_1$-$C_8$ alkoxy.

In some embodiments, $R^3$ is selected from the group consisting of $C_1$-$C_8$ alkyl, $C_1$-$C_8$ alkoxy, $C_1$-$C_8$ alkyl($C_1$-$C_8$alkylene)oxy, $C_5$-$C_{12}$ aryl and $C_5$-$C_{12}$ aryl($C_1$-$C_8$alkylene)oxy.

In some embodiments, $R^3$ is selected from the group consisting of methyl, ethyl and propyl.

In some embodiments, $R^4$ and $R^5$ are each independently selected from the group consisting of hydrogen, hydroxy, $C_1$-$C_8$ alkyl, halogen substituted $C_1$-$C_8$ alkyl, $C_1$-$C_8$ alkoxy, $C_1$-$C_8$ alkylthio, cyano, $C_3$-$C_{10}$ cycloalkyl, ($C_1$-$C_8$ alkylene) $C_3$-$C_{10}$ cycloalkyl, $C_3$-$C_{10}$ cycloalkyl($C_1$-$C_8$ alkylene)oxy, $C_3$-$C_{10}$ cycloalkyloxy, $C_5$-$C_{12}$ aryl, $C_5$-$C_{12}$ aryloxy and $C_5$-$C_{12}$ aryl($C_1$-$C_8$ alkylene)oxy.

In some embodiments, $R^4$ and $R^3$ are each independently selected from the group consisting of $C_1$-$C_8$ alkoxy, halogen substituted $C_1$-$C_8$ alkoxy and $C_5$-$C_{12}$ aryloxy.

In some embodiments, $R^4$ and $R^5$ are each independently selected from the group consisting of methoxy, difluoromethoxy, trifluoromethoxy, ethoxy, propoxy and benzyloxy.

In some embodiments, $R^8$ is selected from the group consisting of hydrogen, $C_1$-$C_8$ alkyl, halogen substituted $C_1$-$C_8$ alkyl, ($C_1$-$C_8$ alkyl substituted amino) substituted $C_1$-$C_8$ alkyl and $C_3$-$C_{12}$ heterocycloalkyl substituted $C_1$-$C_8$ alkyl.

In some embodiments, $R^8$ is selected from the group consisting of hydrogen, methyl, ethyl, dimethylaminomethyl, diethylaminomethyl, piperidylmethyl and morpholinylmethyl.

In some embodiments, a compound of formula (I) is selected from the group consisting of:

N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide, 1-amino-5-(1-(3-ethoxy-4-methoxyphenyl)-2-(methylsulfonyl)ethyl)-5H-thiophene[3,4-c]pyrrole-4,6-diketone, (S)—N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide, (R)—N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide, 5-(1-(3-ethoxy-4-methoxyphenyl)-2-(methylsulfonyl)ethyl)-1-nitro-5H-thiophene[3,4-c]pyrrole-4,6-diketone, N-(5-(1-(3-methoxy-4-ethoxyphenyl)-2-(methylsulfonyl)ethyl)-4,6-dioxo-5,6-dihydro-4H-thiophene[3,4-c]pyrrole-1-yl)acetamide, N-(5-(1-(3,4-dimethoxyphenyl)-2-(methylsulfonyl)ethyl)-4,6-dioxo-5,6-dihydro-4H-thiophene[3,4-c]pyrrole-1-yl)acetamide, 5-(1-(3-ethoxy-4-methoxyphenyl)-2-(methylsulfonyl)ethyl)-5H-thiophene[3,4-c]pyrrole-4,6-diketone, (S)-5-(1-(3-ethoxy-4-methoxyphenyl)-2-(methylsulfonyl)ethyl)-5H-thiophene[3,4-c]pyrrole-4,6-diketone, (R)-5-(1-(3-ethoxy-4-methoxyphenyl)-2-(methylsulfonyl)ethyl)-5H-thiophene[3,4-c]pyrrole-4,6-diketone, (S)-5-(1-(3-methoxy-4-ethoxyphenyl)-2-(methylsulfonyl)ethyl)-5H-thiophene[3,4-c]pyrrole-4,6-diketone, (S)-5-(1-(3,4-dimethoxyphenyl)-2-(methylsulfonyl)ethyl)-5H-thiophene[3,4-e]pyrrole-4,6-diketone, 5-(1-(3-phenylmethoxy-4-methoxyphenyl)-2-(methylsulfonyl)ethyl)-5H-thiophene[3,4-c]pyrrole-4,6-diketone, 5-(1-(3-phenylmethoxy-4-methoxyphenyl)-2-(methylsulfonyl)ethyl)-1-nitro-5 H-thiophene[3,4-c]pyrrole-4,6-diketone, 5-(1-(3-phenylmethoxy-4-methoxyphenyl)-2-(methylsulfonyl)ethyl)-1-amino-5H-thiophene[3,4-c]pyrrole-4,6-diketone, N-(5-(1-(3-phenylmethoxy-4-methoxyphenyl)-2-(methylsulfonyl)ethyl)-4,6-dioxo-5,6-dihydro-4H-thiophene[3,4-c]pyrrole-1-yl)acetamide, 5-(1-(3,4-dimethoxyphenyl)-2-(methylsulfonyl)ethyl)-1-nitro-5H-thiophene[3,4-c]pyrrole-4,6-diketone, 5-(1-(3,4-dimethoxyphenyl)-2-(methylsulfonyl)ethyl)-1-amino-5H-thiophene[3,4-c]pyrrole-4,6-diketone, 5-(1-(3-methoxy-4-ethoxyphenyl)-2-(methylsulfonyl)ethyl)-1-nitro-5H-thiophene[3,4-c]pyrrole-4,6-diketone, 5-(1-(3-methoxy-4-ethoxyphenyl)-2-(methylsulfonyl)ethyl)-1-amino-5H-thiophene[3,4-c]pyrrole-4,6-diketone, 5-(1-(3-ethoxy-4-methoxyphenyl)-2-(methylsulfonyl)ethyl)-1-methylamino-5 H-thiophene[3,4-c]pyrrole-4,6-diketone, 2-chloro-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide, N-(5-(1-(3-ethoxy-4-methoxyphenyl)-2-(methylsulfonyl)ethyl)-4,6-diketone-5,6-dihydro-4H-thiophene[3,4-c]pyrrole-1-yl)methanesulfonamide, (S)-1-amino-5-(1-(3-ethoxy-4-methoxyphenyl)-2-(methylsulfonyl)ethyl)-5H-thiophene[3,4-c]pyrrole-4,6-diketone, (R)-1-amino-5-(1-(3-ethoxy-4-methoxyphenyl)-2-(methylsulfonyl)ethyl)-5H-thiophene[3,4-c]pyrrole-4,6-diketone, N-(5-(1-(3-ethoxy-4-difluoromethoxyphenyl)-2-(methylsulfonyl)ethyl)-4,6-dioxo-5,6-dihydro-4H-thiophene[3,4-c]pyrrole-1-yl)acetamide, N-(5-(1-(3-ethoxy-4-trifluoromethoxyphenyl)-2-(methylsulfonyl)ethyl)-4,6-dioxo-5,6-dihydro-4H-thiophene[3,4-c]pyrrole-1-yl)acetamide, (S)—N-(5-(1-(3-ethoxy-4-difluoromethoxyphenyl)-2-(methylsulfonyl)ethyl)-4,6-dioxo-5,6-dihydro-4H-thiophene[3,4-c]pyrrole-1-yl)acetamide, (R)—N-(5-(1-(3-ethoxy-4-difluoromethoxyphenyl)-2-(methylsulfonyl)ethyl)-4,6-dioxo-5,6-dihydro-4H-thiophene[3,4-c]pyrrole-1-yl)acetamide, (S)—N-(5-(1-(3-ethoxy-4-trifluoromethoxyphenyl)-2-(methylsulfonyl)ethyl)-4,6-dioxo-5,6-dihydro-4H-thiophene[3,4-c]pyrrole-1-yl)acetamide, (R)—N-(5-(1-(3-ethoxy-4-trifluoromethoxyphenyl)-2-(methylsulfonyl)ethyl)-4,6-dioxo-5,6-dihydro-4H-thiophene[3,4-c]pyrrole-1-yl)acetamide, N-(5-(1-(3-phenylmethoxy-4-methoxyphenyl)-2-(methylsulfonyl)ethyl)-4,6-dioxo-5,6-dihydro-4H-thiophene[3,4-c]pyrrole-1-yl)propionamide, 2-(dimethylamino)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide, 2-(diethylamino)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide,
2-(piperidyl)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide, and
2-(morpholinyl)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide.

In another aspect, the present application relates to a process for preparing a compound of formula (I), comprising reacting a compound of formula (A-IV) with a compound of formula (A-VII) to obtain the compound of formula (I):

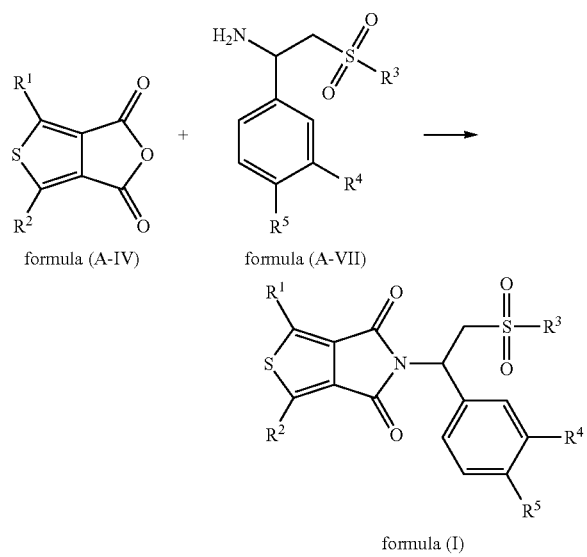

wherein, $R^1$ and $R^2$ are each independently selected from the group consisting of hydrogen, halogen, optionally substituted alkyl, optionally substituted alkoxy, hydroxy, cyano, nitro and optionally substituted $NR^6R^7$;

$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;

$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;

$R^6$ and $R^7$ are each independently selected from the group consisting of hydrogen, optionally substituted alkyl, optionally substituted aryl, optionally substituted $C(O)R^8$ and optionally substituted $SO_2R^8$, or $R^6$ and $R^7$ together represent optionally substituted 1,4-butylidene, optionally substituted 1,5-pentylidene, optionally substituted 1,6-hexylidene or optionally substituted $CH_2CH_2XCH_2CH_2$, wherein X is selected from the group consisting of O, S and $NR^8$;

$R^8$ is selected from the group consisting of hydrogen and optionally substituted alkyl.

In some embodiments, a tertiary amine is added as a catalyst in the process of reacting a compound of formula (A-IV) with a compound of formula (A-VII) to obtain a compound of formula (I).

Appropriate examples of a catalyst that can be used in the present application include, but are not limited to, pyridine, 4-dimethylamino pyridine, 4-pyrrolidinyl pyridine and a mixture thereof.

In some embodiments, a dehydrating agent can further be added in the process of reacting a compound of formula (A-IV) with a compound of formula (A-VII) to obtain a compound of formula (I).

Appropriate examples of a dehydrating agent that can be used in the present application include, but are not limited to, DCC, EDC•HCl, CDI, DIC, azodicarboxylic acid diethyl ester, azodicarboxylic acid diisopropyl ester, azodicarboxylic acid dibenzyl ester and a mixture thereof.

In some embodiments, an activating agent can further be added in the process of reacting a compound of formula (A-IV) with a compound of formula (A-VII) to obtain a compound of formula (I).

Appropriate examples of an activating agent that can be used in the present application include, but are not limited to, N-hydroxy succinimide, HOBt, HOAt, BOP, Cl-HOBt, DEPBT, HATU, HBTU, HCTU, HOOBt, PyBOP, TATU, TBTU and a mixture thereof.

In some embodiments, the process of reacting a compound of formula (A-IV) with a compound of formula (A-VII) is carried out in an organic solvent to obtain a compound of formula (I).

Appropriate examples of an organic solvent that can be used in the present application include, but are not limited to, chloroform, dichloromethane, dichloroethane, tetrahydrofuran, diethyl ether, isopropyl ether, ethyl acetate, glycol dimethyl ether, glycol diethyl ether, benzene, toluene, n-hexane, cyclohexane, DMF, DMSO, methyl ethyl ether, methyl propyl ether, methyl t-butyl ether, acetone, butanone, methyl formate, ethyl formate, propyl formate, butyl formate, methyl acetate, propyl acetate, butyl acetate and a mixture thereof.

In some embodiments, the reaction of a compound of formula (A-IV) with a compound of formula (A-VII) is carried out at −10° C.-200° C. to obtain a compound of formula (I).

In some embodiments, the reaction of a compound of formula (A-IV) with a compound of formula (A-VII) is carried out at −10° C.-150° C. to obtain a compound of formula (I).

In some embodiments, dehydration of a compound of formula (A-III) is carried out to obtain a compound of formula (A-IV),

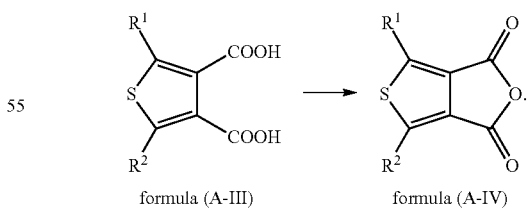

Appropriate examples of a dehydrating agent that can be used in the present application include, but are not limited to, acetic anhydride, trifluoroacetic anhydride and a mixture thereof.

In some embodiments, dehydration of a compound of formula (A-III) is carried out in an organic solvent to obtain a compound of formula (A-IV).

Appropriate examples of an organic solvent that can be used in the present application include, but are not limited to, chloroform, dichloromethane, dichloroethane, tetrahydrofuran, diethyl ether, isopropyl ether, cyclohexane, n-hexane, ethyl acetate, glycol dimethyl ether, glycol diethyl ether, benzene, toluene, DMF, DMSO, acetone, butanone, methyl ethyl ether, methyl t-butyl ether, methyl propyl ether, methyl formate, ethyl formate, propyl formate, butyl formate, methyl acetate, propyl acetate, butyl acetate, acetic acid, trifluoroacetic acid and a mixture thereof.

In some embodiments, a compound of formula (A-III) is obtained with a compound of formula (A-II) in the presence of an acid or a base,

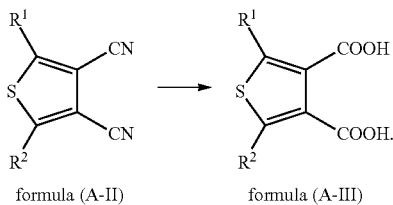

formula (A-II)    formula (A-III)

Appropriate examples of a base that can be used in the present application include, but are not limited to, sodium hydroxide, potassium hydroxide, lithium hydroxide and a mixture thereof.

Appropriate examples of an acid that can be used in the present application include, but are not limited to, hydrochloric acid, sulfuric acid, phosphoric acid, methanesulfonic acid, ethanesulfonic acid and a mixture thereof. In some embodiments, a compound of formula (A-III) is obtained with a compound of formula (A-II) in a solvent in the presence of an acid or a base.

Appropriate examples of a solvent that can be used in the present application include, but are not limited to, chloroform, dichloromethane, dichloroethane, tetrahydrofuran, diethyl ether, isopropyl ether, cyclohexane, n-hexane, ethyl acetate, glycol dimethyl ether, glycol diethyl ether, benzene, toluene, DMF, DMSO, acetone, butanone, methyl ethyl ether, methyl t-butyl ether, methyl propyl ether, methyl formate, ethyl formate, propyl formate, butyl formate, methyl acetate, propyl acetate, butyl acetate, acetic acid, trifluoroacetic acid, water and a mixture thereof.

In some embodiments, a compound of formula (A-III) is obtained with a compound of formula (A-II) at 0° C.-200° C. in the presence of an acid or a base.

In some embodiments, a compound of formula (A-III) is obtained with a compound of formula (A-II) at 50° C.-200° C. in the presence of an acid or a base.

In some embodiments, a compound of formula (A-III) is obtained with a compound of formula (A-II) at 80° C.-180° C. in the presence of an acid or a base.

In some embodiments, the reaction of a compound of formula (A-I) with a cyanide is carried out to obtain a compound of formula (A-II),

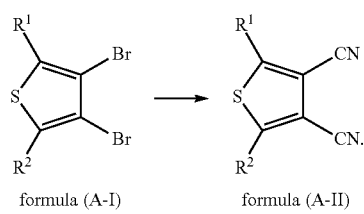

formula (A-I)    formula (A-II)

Appropriate examples of a cyanide that can be used in the present application include, but are not limited to, cuprous cyanide, sodium cyanide, potassium cyanide and mercury cyanide.

In some embodiments, the reaction of a compound of formula (A-I) with a cyanide is carried out in an organic solvent to obtain a compound of formula (A-II).

Appropriate examples of an organic solvent that can be used in the present application include, but are not limited to, DMF, DMSO, acetamide, N-methylpyrrolidone, diethylene glycol dimethyl ether, diethylene glycol diethyl ether and a mixture thereof.

In some embodiments, the reaction of a compound of formula (A-I) with a cyanide is carried out at 50° C.-250° C. to obtain a compound of formula (A-II).

In some embodiments, the reaction of a compound of formula (A-I) with a cyanide is carried out at 100° C.-250° C. to obtain a compound of formula (A-II).

In some embodiments, a compound of formula (A-VII) is obtained by reacting a compound of formula (A-VI) in the presence of a deprotective agent,

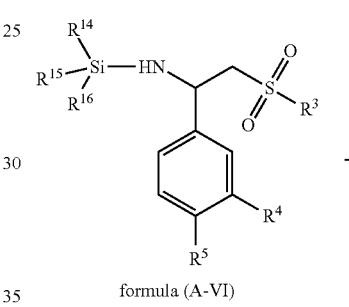

formula (A-VI)

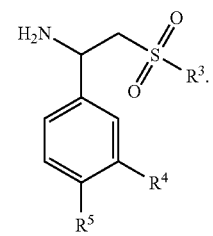

formula (A-VII)

Appropriate examples of a deprotective agent that can be used in the present application include, but are not limited to, tetrabutylammonium floride, tetraethylammonium floride, hydrochloric acid, sulfuric acid, phosphoric acid, nitric acid, acetic acid, trifluoroacetic acid, formic acid, methanesulfonic acid, ethanesulfonic acid, benzenesulfonic acid, p-toluenesulfonic acid and a mixture thereof.

In some embodiments, a compound of formula (A-VII) is obtained by reacting a compound of formula (A-VI) in the presence of a deprotective agent in a solvent.

Appropriate examples of a solvent that can be used in the present application include, but are not limited to, chloroform, dichloromethane, dichloroethane, tetrahydrofuran, diethyl ether, isopropyl ether, ethyl acetate, ethanol, methanol, propyl alcohol, butyl alcohol, ethylene glycol, glycol dimethyl ether, ethylene glycol monomethyl ether, ethylene glycol monoethyl ether, glycol diethyl ether, benzene, toluene, n-hexane, cyclohexane, DMF, DMSO, acetic acid, trifluoroacetic acid, methyl ethyl ether, methyl propyl ether, methyl t-butyl ether, acetone, butanone, methyl formate, ethyl formate, propyl formate, butyl formate, methyl acetate, propyl acetate, butyl acetate, water and a mixture thereof.

In some embodiments, a compound of formula (A-VII) is obtained by reacting a compound of formula (A-VI) in the presence of a deprotective agent at −20° C.-200° C.

In some embodiments, a compound of formula (A-VII) is obtained by reacting a compound of formula (A-VI) in the presence of a deprotective agent at 0° C.-200° C.

In some embodiments, the reaction of a compound of formula (A-V) with $CH_3S(O)_2R^3$ and $(R^{14}R^{15}R^{16}Si)_2NM$ is carried out in the presence of a strong base to obtain a compound of formula (A-VII),

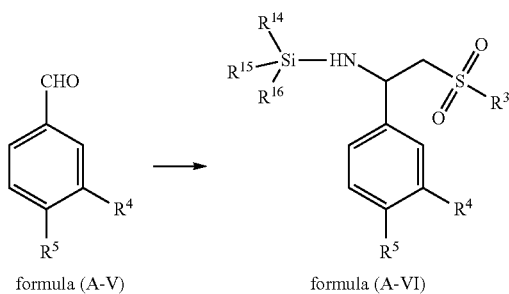

formula (A-V)　　　　formula (A-VI)

wherein the group represented by $R^3$ in $CH_3S(O)_2R^3$ is identical to the group represented by $R^3$ in the compound of formula (I), and wherein $R^{14}$, $R^{15}$ or $R^{16}$ in $(R^{14}R^{15}R^{16}Si)_2NM$ are each independently selected from the group consisting of alkyl and phenyl, and M is selected from the group consisting of sodium, potassium and lithium.

Appropriate examples of a strong base that can be used in the present application include, but are not limited to, alkyl lithium, alkyl sodium, alkyl potassium, sodium alkoxide, potassium alkoxide, lithium alkoxide, alkyl sodium amide, alkyl lithium amide and alkyl potassium amide.

In some embodiments, appropriate examples of a strong base that can be used in the present application include, but are not limited to, n-butyl lithium, t-butyl lithium, methyl lithium, ethyl lithium, sodium methoxide, potassium methoxide, lithium methoxide, lithium dimethylamide, lithium diethylamide, lithium dipropylamide, lithium diisopropylamide and a mixture thereof.

Appropriate examples of $(R^{14}R^{15}R^{16}Si)_2NM$ that can be used in the present application include, but are not limited to, lithium bis(trimethylsilyl)amide, lithium bis(triethylsilyl)amide, lithium bis(tripropylsilyl)amide, lithium bis(triisopropylsilyl)amide, lithium bis(dimethylethylsilyl)amide, lithium bis(dimethylpropylsilyl)amide, lithium bis(dimethylisopropylsilyl)amide, lithium bis(dimethylphenylsilyl)amide, lithium bis(dimethylbenzylsilyl)amide, lithium bis(diethylmethylsilyl)amide, lithium bis(diethylpropylsilyl)amide, lithium bis(diethylisopropylsilyl)amide, lithium bis(diethylphenylsilyl)amide, lithium bis(diethylbenzylsilyl)amide, lithium bis(diisopropylmethylsilyl)amide, lithium bis(diisopropylethylsilyl)amide, lithium bis(diisopropylphenylsilyl)amide, lithium bis(diisopropylbenzylsilyl)amide, sodium bis(trimethylsilyl)amide, sodium bis(triethylsilyl)amide, sodium bis(tripropylsilyl)amide, sodium bis(triisopropylsilyl)amide, sodium bis(dimethylethylsilyl)amide, sodium bis(dimethylpropylsilyl)amide, sodium bis(dimethylisopropylsilyl)amide, sodium bis(dimethylphenylsilyl)amide, sodium bis(dimethylbenzylsilyl)amide, sodium bis(diethyl methylsilyl)amide, sodium bis(diethylpropylsilyl)amide, sodium bis(diethylisopropylsilyl)amide, sodium bis(diethylphenylsilyl)amide, sodium bis(diethylbenzylsilyl)amide, sodium bis(diisopropylmethylsilyl)amide, sodium bis(diisopropylethylsilyl)amide, sodium bis(diisopropylphenylsilyl)amide, sodium bis(diisopropylbenzylsilyl)amide, potassium bis(trimethylsilyl)amide, potassium bis(triethylsilyl)amide, potassium bis(tripropylsilyl)amide, potassium bis(triisopropylsilyl)amide, potassium bis(dimethyl ethylsilyl)amide, potassium bis(dimethylpropylsilyl)amide, potassium bis(dimethylisopropylsilyl)amide, potassium bis(dimethylphenylsilyl)amide, potassium bis(dimethylbenzylsilyl)amide, potassium bis(diethyl methylsilyl)amide, potassium bis(diethylpropylsilyl)amide, potassium bis(diethylisopropylsilyl)amide, potassium bis(diethylphenylsilyl)amide, potassium bis(diethylbenzylsilyl)amide, potassium bis(diisopropylmethylsilyl)amide, potassium bis(diisopropylethylsilyl)amide, potassium bis(diisopropylphenylsilyl)amide and potassium bis(diisopropylbenzylsilyl)amide.

In some embodiments, the reaction of a compound of formula (A-V) with $CH_3S(O)_2R^3$ and $(R^{14}R^{15}R^{16}Si)_2NM$ is carried out with a catalyst in the presence of a strong base to obtain a compound of formula (A-VII).

Appropriate examples of a catalyst that can be used in the present application include, but are not limited to, fluorinating agent.

Appropriate examples of a fluorinating agent that can be used in the present application include, but are not limited to, boron trifluoride.

In some embodiments, the reaction of a compound of formula (A-V) with $CH_3S(O)_2R^3$ and $(R^{14}R^{15}R^{16}Si)_2NM$ is carried out in the presence of a strong base at −100° C.-100° C. to obtain a compound of formula (A-VII).

In some embodiments, the reaction of a compound of formula (A-V) with $CH_3S(O)_2R^3$ and $(R^{14}R^{15}R^{16}Si)_2NM$ is carried out in the presence of a strong base at −100° C.-50° C. to obtain a compound of formula (A-VII).

In another aspect, the present application relates to a process for preparing a compound of formula (B-III), comprising reacting a compound of formula (B-II) with a compound of formula $R^{11}$—Y, $(R^{12})_2$Y or Y—$R^{13}$—Z to obtain the compound of formula (B-III),

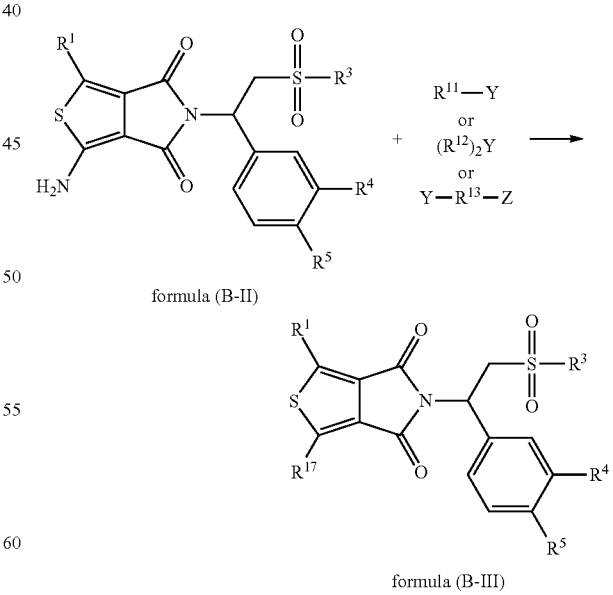

formula (B-II)

formula (B-III)

wherein, $R^1$ is selected from the group consisting of hydrogen, halogen, $C_1$-$C_8$ alkyl, $C_1$-$C_8$ alkoxy, hydroxy, cyano, nitro and $NR^6R^7$;

$R^3$ is selected from the group consisting of hydroxy, $C_1$-$C_8$ alkyl, $C_1$-$C_8$ alkoxy, $C_1$-$C_8$ alkyl($C_1$-$C_8$ alkylene)oxy, $C_5$-$C_{12}$ aryl, $C_5$-$C_{12}$ aryl($C_1$-$C_8$ alkylene)oxy and $NR^6R^7$;

$R^4$ and $R^5$ are each independently selected from the group consisting of hydrogen, hydroxy, $C_1$-$C_8$ alkyl, $C_1$-$C_8$ alkoxy, $C_1$-$C_8$ alkylthio, cyano, $C_3$-$C_{10}$ cycloalkyl, ($C_1$-$C_8$ alkylene) $C_3$-$C_{10}$ cycloalkyl, $C_3$-$C_{10}$ cycloalkyl($C_1$-$C_8$ alkylene)oxy, $C_3$-$C_{10}$ cycloalkyloxy, $C_5$-$C_{12}$ aryl, $C_5$-$C_{12}$ aryloxy and $C_5$-$C_{12}$ aryl($C_1$-$C_8$ alkylene)oxy;

$R^6$ and $R^7$ are each independently selected from the group consisting of hydrogen, $C_1$-$C_8$ alkyl, aryl, $C(O)R^8$ and $SO_2R^8$, or $R^6$ and $R^7$ together represent 1,4-butylidene, 1,5-pentylidene, 1,6-hexylidene or $CH_2CH_2XCH_2CH_2$, wherein X is selected from the group consisting of O, S and $NR^8$;

$R^8$ is selected from the group consisting of hydrogen and halogen substituted $C_1$-$C_8$ alkyl;

$R^{11}$ in $R^{11}$—Y is selected from the group consisting of $C_1$-$C_8$ alkyl, $C_5$-$C_{12}$ aryl, $C(O)R^8$ and $S(O)_2R^8$, Y is selected from the group consisting of halogen, OMs and OTs;

$R^{12}$ in $(R^{12})_2Y$ is selected from $C(O)R^8$, and Y is O;

$R^{13}$ in Y—$R^{13}$—Z is selected from the group consisting of 1,4-butylidene, 1,5-pentylidene, 1,6-hexylidene and $CH_2CH_2XCH_2CH_2$, Y and Z are each independently selected from the group consisting of halogen, OMs and OTs, X represents O, S or $NR^8$.

In some embodiments, an alkaline reagent is added to the reaction of a compound of formula (B-II) with a compound of formula $R^{11}$—Y, $(R^{12})_2Y$ or Y—$R^{13}$—Z to obtain a compound of formula (B-II).

Appropriate examples of an alkaline reagent that can be used in the present application include, but are not limited to, triethylamine, trimethylamine, tripropylamine, diisopropyl ethylamine, pyridine, N-methylmorpholine, N-ethylmorpholine, N-methylpiperidine, N-ethylpiperidine, N-methylpyrrolidine, N-ethylpyrrolidine, 4-dimethylamino pyridine, 4-pyrrolidinyl pyridine, 2-methylpyridine, 3-methylpyridine, 4-methylpyridine, 2,6-dimethylpyridine, 2,4,6-trimethylpyridine, sodium hydroxide, potassium hydroxide, lithium hydroxide, sodium carbonate, potassium carbonate, lithium carbonate, cesium carbonate, sodium hydride, potassium hydride, lithium hydride, aluminium lithium hydride, sodium methoxide, potassium methoxide, lithium methoxide, sodium ethoxide, potassium ethoxide, lithium ethoxide, sodium isopropylate, potassium isopropylate, lithium isopropylate, $(R^{14}R^{15}R^{16}Si)_2NM$, sodium amide, lithium amide, potassium amide and a mixture thereof, wherein $R^{14}$, $R^{15}$ and $R^{16}$ in $(R^{14}R^{15}R^{16}Si)_2NM$ are each independently selected from the group consisting of $C_{1-8}$ alkyl and phenyl, M is selected from the group consisting of sodium, potassium and lithium.

Appropriate examples of $(R^{14}R^{15}R^{16}Si)_2NM$ that can be used in the present application include, but are not limited to, lithium bis(trimethylsilyl)amide, lithium bis(triethylsilyl)amide, lithium bis(tripropylsilyl)amide, lithium bis(triisopropylsilyl)amide, lithium bis(dimethyl ethylsilyl)amide, lithium bis(dimethylpropylsilyl)amide, lithium bis(dimethylisopropylsilyl)amide, lithium bis(dimethylphenylsilyl)amide, lithium bis(dimethylbenzylsilyl)amide, lithium bis(diethylmethylsilyl)amide, lithium bis(diethylpropylsilyl)amide, lithium bis(diethylisopropylsilyl)amide, lithium bis(diethylphenylsilyl)amide, lithium bis(diethylbenzylsilyl)amide, lithium bis(diisopropylmethylsilyl)amide, lithium bis(diisopropylethylsilyl)amide, lithium bis(diisopropylphenylsilyl)amide, lithium bis(diisopropylbenzylsilyl)amide, sodium bis trimethylsilyl amide, sodium bis(triethylsilyl)amide, sodium bis(tripropylsilyl)amide, sodium bis(triisopropylsilyl)amide, sodium bis(dimethylethylsilyl)amide, sodium bis(dimethylpropylsilyl)amide, sodium bis(dimethylisopropylsilyl)amide, sodium bis(dimethylphenylsilyl)amide, sodium bis(dimethylbenzylsilyl)amide, sodium bis(diethyl methylsilyl)amide, sodium bis(diethylpropylsilyl)amide, sodium bis(diethylisopropylsilyl)amide, sodium bis(diethylphenylsilyl)amide, sodium bis(diethylbenzylsilyl)amide, sodium bis(diisopropylmethylsilyl)amide, sodium bis(diisopropylethylsilyl)amide, sodium bis(diisopropylphenylsilyl)amide, sodium bis(diisopropylbenzylsilyl)amide, potassium bis(trimethylsilyl)amide, potassium bis(triethylsilyl)amide, potassium bis(tripropylsilyl)amide, potassium bis(triisopropylsilyl)amide, potassium bis(dimethyl ethylsilyl)amide, potassium bis(dimethylpropylsilyl)amide, potassium bis(dimethylisopropylsilyl)amide, potassium bis(dimethylphenylsilyl)amide, potassium bis(dimethylbenzylsilyl)amide, potassium bis(diethylmethylsilyl)amide, potassium bis(diethylpropylsilyl)amide, potassium bis(diethylisopropylsilyl)amide, potassium bis(diethylphenylsilyl)amide, potassium bis(diethylbenzylsilyl)amide, potassium bis(diisopropylmethylsilyl)amide, potassium bis(diisopropylethylsilyl)amide, potassium bis(diisopropylphenylsilyl)amide and potassium bis(diisopropylbenzylsilyl)amide.

In some embodiments, the reaction of a compound of formula (B-II) with a compound of formula $R^{11}$—Y, $(R^{12})_2Y$ or Y—$R^{13}$—Z is carried out in a solvent to obtain a compound of formula (B-II).

Appropriate examples of a solvent that can be used in the present application include, but are not limited to, chloroform, dichloromethane, dichloroethane, tetrahydrofuran, acetone, butanone, methyl acetate, propyl acetate, butyl acetate, isopropyl acetate, methyl formate, ethyl formate, propyl formate, butyl formate, isopropyl formate, methyl propionate, ethyl propionate, propyl propionate, butyl propionate, isopropyl propionate, methyl ether, diethyl ether, methyl diethyl ether, methyl t-butyl ether, ethyl t-butyl ether, methyl isopropyl ether, ethyl isopropyl ether, isopropyl ether, ethyl acetate, ethanol, methanol, propyl alcohol, butyl alcohol, ethylene glycol, glycol dimethyl ether, ethylene glycol monomethyl ether, ethylene glycol monoethyl ether, glycol diethyl ether, benzene, toluene, n-hexane, cyclohexane, DMF, DMSO, petroleum ether, water and a mixture thereof.

In some embodiments, the reaction of a compound of formula (B-II) with a compound of formula $R^{11}$—Y, $(R^{12})_2Y$ or Y—$R^{13}$—Z is carried out at −20° C.-200° C. to obtain a compound of formula (B-II).

In some embodiments, the reaction of a compound of formula (B-II) with a compound of formula $R^{11}$—Y, $(R^{12})_2Y$ or Y—$R^{13}$—Z is carried out at −10° C.-100° C. to obtain a compound of formula (B-II).

In some embodiments, a compound of formula (B-II) is prepared with a compound of formula (B-I),

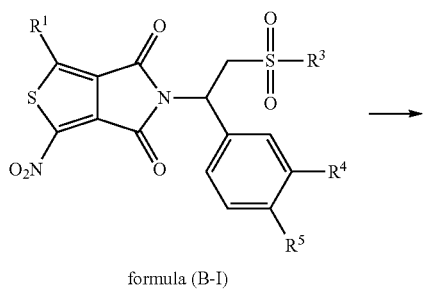

formula (B-I)

-continued formula (B-II)

wherein, $R^1$ is selected from the group consisting of hydrogen, halogen, $C_1$-$C_8$ alkyl, $C_1$-$C_8$ alkoxy, hydroxy, cyano, nitro and $NR^6R^7$;

$R^3$ is selected from the group consisting of hydroxy, $C_1$-$C_8$ alkyl, $C_1$-$C_8$ alkoxy, $C_1$-$C_8$ alkyl($C_1$-$C_8$ alkylene)oxy, $C_5$-$C_{12}$ aryl, $C_5$-$C_{12}$ aryl($C_1$-$C_8$ alkylene)oxy and $NR^6R^7$;

$R^4$ and $R^5$ are separately selected from the group consisting of hydrogen, hydroxy, $C_1$-$C_8$ alkyl, $C_1$-$C_8$ alkoxy, $C_1$-$C_8$ alkylthio, cyano, $C_3$-$C_{10}$ cycloalkyl, ($C_1$-$C_8$ alkylene) $C_3$-$C_{10}$ cycloalkyl, $C_3$-$C_{10}$ cycloalkyl ($C_1$-$C_8$ alkylene)oxy, $C_3$-$C_{10}$ cycloalkyloxy, $C_5$-$C_{12}$ aryl, $C_5$-$C_{12}$ aryloxy and $C_5$-$C_{12}$ aryl ($C_1$-$C_8$ alkylene)oxy;

$R^6$ and $R^7$ are each independently selected from the group consisting of hydrogen, $C_1$-$C_8$ alkyl, aryl, $C(O)R^8$ or $SO_2R^8$, or $R^6$ and $R^7$ together represent 1,4-butylidene, 1,5-pentylidene, 1,6-hexylidene and $CH_2CH_2XCH_2CH_2$, wherein X is selected from the group consisting of O, S and $NR^8$;

$R^8$ is selected from the group consisting of hydrogen and halogen substituted $C_1$-$C_8$ alkyl.

In some embodiments, the reaction for preparing a compound of formula (B-II) with a compound of formula (B-I) is carried out in the presence of a reductive agent.

Appropriate examples of a reductive agent that can be used in the present application include, but are not limited to, powdery iron, powdery sodium hydrosulfite, powdery zinc and hydrogen.

In some embodiments, the reaction for preparing a compound of formula (B-II) with a compound of formula (B-I) is carried out in the presence of a catalyst.

Appropriate examples of a catalyst that can be used in the present application include, but are not limited to, heavy metals such as palladium, platinum, rhodium, nickel, ruthenium, iridium, etc., and oxide or salt thereof, such as hydrochloride, sulfuric acid, phosphoric acid, formic acid, acetic acid, propionic acid, methanesulfonic acid, ethanesulfonic acid, benzenesulfonic acid and p-toluenesulfonic acid.

In some embodiments, the reaction for preparing a compound of formula (B-II) with a compound of formula (B-I) is carried out in the presence of the following catalysts hydrochloride, sulfuric acid, phosphoric acid, formic acid, acetic acid, propionic acid, methanesulfonic acid, ethanesulfonic acid, benzenesulfonic acid, p-toluenesulfonic acid, palladium-carbon, platinum-carbon, platinum dioxide, palladium chloride, platinum chloride, raney nickel or a mixture thereof.

In some embodiments, the reaction for preparing a compound of formula (B-II) with a compound of formula (B-I) is carried out in a solvent.

Appropriate examples of a solvent that can be used in the present application include, but are not limited to, methanol, ethanol, propyl alcohol, butyl alcohol, isopropyl alcohol, chloroform, dichloromethane, carbon tetrachloride, 1,2-dichloroethane, glycol dimethyl ether, glycol diethyl ether, diethyl ether, methyl ethyl ether, methyl propyl ether, methyl butyl ether, ethyl propyl ether, methyl t-butyl ether, tetrahydrofuran, ethyl acetate, methyl acetate, propyl acetate, butyl acetate, methyl propionate, ethyl propionate, methyl formate, ethyl formate, propyl formate, isopropyl acetate, acetone, butanone, pyridine, DMF, DMSO, acetonitrile, propionitrile, benzene, toluene, water and a mixture thereof.

In some embodiments, a compound of formula (B-II) is prepared with a compound of formula (B-I) at −20° C.-250° C.

In some embodiments, a compound of formula (B-II) is prepared with a compound of formula (B-I) at 0° C.-150° C.

In some embodiments, a compound of formula (B-II) is prepared with a compound of formula (B-I) at 1 atm-100 atm.

In some embodiments, a compound of formula (B-II) is prepared with a compound of formula (B-I) at 1 atm-20 atm.

In still another aspect, the present application relates to a pharmaceutical composition comprising a pharmaceutically acceptable carrier and a therapeutically effective amount of a compound of formula (I), a stereoisomer, an enantiomer or a tautomer, or a mixture of stereoisomers thereof, a pharmaceutically acceptable salt thereof, a polymorph thereof, a solvate thereof, a prodrug thereof or a metabolite thereof,

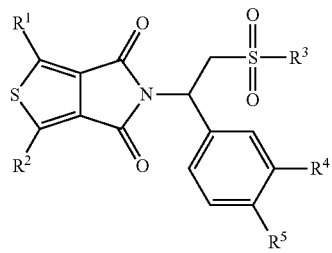

formula (I)

wherein, $R^1$ and $R^2$ are each independently selected from the group consisting of hydrogen, halogen, optionally substituted alkyl, optionally substituted alkoxy, hydroxy, cyano, nitro and optionally substituted $NR^6R^7$;

$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;

$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene) oxy;

$R^6$ and $R^7$ are each independently selected from the group consisting of hydrogen, optionally substituted alkyl, optionally substituted aryl, optionally substituted $C(O)R^8$ and optionally substituted $SO_2R^8$, or $R^6$ and $R^7$ together represent optionally substituted 1,4-butylidene, optionally substituted 1,5-pentylidene, optionally substituted 1,6-hexylidene or optionally substituted $CH_2CH_2XCH_2CH_2$, wherein X is selected from the group consisting of O, S and $NR^8$;

$R^8$ is selected from the group consisting of hydrogen and optionally substituted alkyl.

Examples of a pharmaceutically acceptable carrier, diluent or excipient that can be used in the pharmaceutical composition of the present application include, but are not limited to, any adjuvant, carrier, excipient, glidant, sweetening agent, diluent, preservative, dye/colorant, flavor enchancer, surfactant, wetting agent, dispersing agent, suspending agent, stabilizer, isosmotic agent, solvent or emulsifier, which has been approved by the United States Food and Drug Administration as being acceptable for use in humans or animals.

In some embodiments, the pharmaceutical composition of the present application further comprises at least one another active ingredient.

Appropriate examples of active ingredients that can be used in the present application include, but are not limited to, nitrogen mustard, aziridine, methylmelamine, alkyl sulphonate, nitrosourea, triazene, folacin, pyrimidine analogue, purine analogue, vinca alkaloid, epipodophyllotoxin, antibiotic, topoisomerase inhibitor, anticancer vaccine, acivicin, aclarubicin, acodazole hydrochloride, acronine, adozelesin, aldesleukin, ambomycin, ametantrone acetate, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin, droloxifene hydrochloride, epirubicin hydrochloride, esorubicin hydrochloride, estramustine, etanidazole, etoposide, floxuridine, fluorouracil, fluorocitabine, gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, angiogenesis inhibitor, camptothecin, hexadecadrol, aspirin, acetaminophen, indometacin, ibuprofen, ketoprofen, meloxicam, corticosteroid and adrenal corticosteroid.

In some embodiments, a pharmaceutical composition of the present application is formulated as tablet, solution, granule, patch, ointment, capsule, aerosol or suppository administered via parenteral, transdermal, mucosa, nasal, buccal, sublingual or oral route.

In yet another aspect, the present application relates to a method for reducing activity of PDE4 enzyme, comprising contacting PDE4 enzyme with a therapeutically effective amount of a compound of formula (I), an enantiomer or a tautomer, or a mixture of stereoisomer thereof, a pharmaceutically acceptable salt thereof, a polymorph thereof, a solvate thereof, a prodrug thereof or a metabolite thereof,

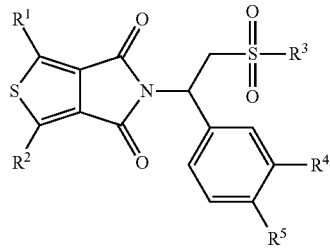

formula (I)

wherein, $R^1$ and $R^2$ are each independently selected from the group consisting of hydrogen, halogen, optionally substituted alkyl, optionally substituted alkoxy, hydroxy, cyano, nitro and optionally substituted $NR^6R^7$;

$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;

$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene) oxy;

$R^6$ and $R^7$ are each independently selected from the group consisting of hydrogen, optionally substituted alkyl, optionally substituted aryl, optionally substituted $C(O)R^8$ and optionally substituted $SO_2R^8$, or $R^6$ and $R^7$ together represent optionally substituted 1,4-butylidene, optionally substituted 1,5-pentylidene, optionally substituted 1,6-hexylidene or optionally substituted $CH_2CH_2XCH_2CH_2$, wherein X is selected from the group consisting of O, S and $NR^8$;

$R^8$ is selected from the group consisting of hydrogen and optionally substituted alkyl.

In some embodiments, contacting PDE4 enzyme with a therapeutically effective amount of a compound of formula (I), an enantiomer or a tautomer, or a mixture of stereoisomer thereof, a pharmaceutically acceptable salt thereof, a polymorph thereof, a solvate thereof, a prodrug thereof or a metabolite thereof is carried out in vitro.

In still another aspect, the present application further relates to a method for treating diseases or conditions mediated by PDE4 enzyme, comprising administering to a subject in need thereof a therapeutically effective amount of a compound of formula (I), a stereoisomer, an enantiomer or a tautomer, or a mixture of stereoisomer thereof, a pharmaceutically acceptable salt thereof, a polymorph thereof, a solvate thereof, a prodrug thereof or a metabolite thereof,

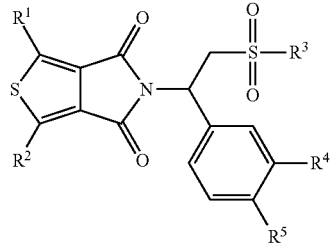

formula (I)

wherein, $R^1$ and $R^2$ are each independently selected from the group consisting of hydrogen, halogen, optionally substituted alkyl, optionally substituted alkoxy, hydroxy, cyano, nitro and optionally substituted $NR^6R^7$;

$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;

$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene) oxy;

$R^6$ and $R^7$ are each independently selected from the group consisting of hydrogen, optionally substituted alkyl, optionally substituted aryl, optionally substituted $C(O)R^8$ and optionally substituted $SO_2R^8$, or $R^6$ and $R^7$ together represent optionally substituted 1,4-butylidene, optionally substituted 1,5-pentylidene, optionally substituted 1,6-hexylidene or optionally substituted $CH_2CH_2XCH_2CH_2$, wherein X is selected from the group consisting of O, S and $NR^8$;

$R^8$ is selected from the group consisting of hydrogen and optionally substituted alkyl.

In some embodiments, the diseases or conditions are selected from the group consisting of inflammatory diseases or conditions, infectious diseases or conditions, immune diseases or conditions, and cancer diseases or conditions.

In some embodiments, examples of the diseases or conditions include, but are not limited to, head carcinoma, thyroid carcinoma, neck cancer, eye cancer, skin cancer, oral cancer, throat cancer, esophagus cancer, breast cancer, bone cancer, leukemia, myeloma, lung cancer, colon cancer, carcinomaofsigmoid, rectal cancer, gastric cancer, prostate cancer, breast cancer, ovarian cancer, kidney cancer, liver cancer, pancreatic cancer, brain cancer, intestinal cancer, heart cancer, adrenal carcinoma, subcutaneous tissue cancer, lymph node cancer, malinant melanoma, malignant glioma, HIV, hepatitis, adult respiratory distress syndrome, bone absorption disease, chronic obstructive pulmonary disease, chronic pneumonia, dermatitis, inflammatory skin disease, atopic dermatitis, cysticfibrosis, septic shock, pyaemia, endotoxin shock, blood dynamic shock, septic disease syndrome, ischemia reperfusion injury, meningitis, psoriasis, fibrosis disease, cachexia, graft rejection of graft versus host disease, autoimmunity disease, rheumatoidspondylitis, arthritis symptom (such as rheumatoid arthritis or osteoarthritis), osteoporosis, Crohn's disease, ulcerative colitis, enteritis, multiple sclerosis, systemic lupus erythematosus, erythema nodosum leprosum of leprosy (ENL), radiation damage, asthma, oxygen enriched lung injury, microorganism infections and microorganism infection syndrome.

In some embodiments, examples of microorganism infection and microorganism infective syndrome mediated by PDE4 enzyme to be treated in the present application include, but are not limited to, bacterial infections, fungus infections, malaria, mycobacteria infections and opportunistic infections induced by HIV.

In some embodiments, a subject in need of the method for treating diseases or conditions mediated by PDE4 enzyme is administered a unit dose of 0.1 mg-1000 mg of a compound of formula (I).

In some embodiments, a subject in need of the method for treating diseases or conditions mediated by PDE4 enzyme is administered a unit dose of 1 mg-1000 mg of a compound of formula (I).

In some embodiments, a method for treating diseases or conditions mediated by PDE4 enzyme further comprises administering a subject in need thereof at least another active ingredient.

Appropriate examples of active ingredients that can be used in the present application include, but are not limited to, nitrogen mustard, aziridine, methylmelamine, alkyl sulphonate, nitrosourea, triazene, folacin, pyrimidine analogue, purine analogue, vinca alkaloid, epipodophyllotoxin, antibiotic, topoisomerase inhibitor, anticancer vaccine, acivicin, aclarubicin, hydrochloride acodazole, acronine, adozelesin, aldesleukin, ambomycin, acetate ametantrone, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin hydrochloride, droloxifene, epirubicin hydrochloride, esorubicin hydrochloride, estramustine, etanidazole, etoposide, floxuridine, fluorouracil, fluorocitabine, gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, angiogenesis inhibitor, camptothecin, hexadecadrol, aspirin, acetaminophen, indometacin, ibuprofen, ketoprofen, meloxicam, corticosteroid and adrenal corticosteroid.

In some embodiments, a subject in need of the method for treating diseases or conditions mediated by PDE4 enzyme is simultaneously, concurrently, separately or sequentially administered a compound of formula (I) and at least another active ingredient.

EXAMPLES

Although anyone skilled in the art is capable of preparing the compounds of the present application according to the general techniques disclosed above, more specific details on synthetic techniques for compound of the present application are provided elsewhere in this specification for convenience. Again, all reagents and reaction conditions employed in synthesis are known to those skilled in the art and are available from ordinary commercial sources.

ABBREVIATIONS

CDI: 1,1'-carbonyldiimidazole;
DCM: dichloromethane;
THF: tetrahydrofuran;
TFA: trifluoroacetic acid;
DMAP: 4-(N,N-dimethylamino)pyridine;
TEA: triethylamine;
DMF: N,N-dimethylfomiamide;
DMSO: dimethylsulfoxide;
HOBt: 1-hydroxybenzotriazole;
DCC: N,N-dicyclohexyl carbondiimide;
TBFA: tetrabutylammonium floride;
EDC•HCl: 1-(3-dimethylaminopropyl)-3-ethyl carbodiimide hydrochloride;
Fmoc: 9-fluorenylmethoxycarbonyl;
MOM: methoxymethyl;
MEM: methoxy ethoxy methyl;
MTM: methylthiomethyl;
SEM: 2-(trimethylsilyl)ethoxy methyl;
TMSE: 2-(trimethylsilyl)ethyl;
DIC: N,N'-diisopropyl carbodiimide;
HOAt: 1-hydroxy-7-azobenzotriazole;
BOP: (benzotriazole-1-yl-oxy-tri-(dimethylamino)phosphonium hexafluoro phosphate);
Cl-HOBt: 6-chloro-1-hydroxy benzotriazole;
DEPBT: 3-(diethoxyphosphoryloxy)-1,2,3-phentriazine-4-one;
HATU: bis(dimethylamino)methylene-triazole[4,5-B]pyridine-3-oxidehexafluorophosphate;

HBTU: benzotriazole-N,N,N',N'-tetramethylurea-hexafluorophosphate;
HCTU: 6-chlorobenzotriazole-1,1,3,3-tetramethylurea-hexafluorophosphate;
HOOBt: 3-hydroxy-1,2,3-phentriazine-4(3H)-one;
PyBOP: hexafluorophosphoric acid benzotriazole-1-yloxy tripyrrolidinylphosphine;
TATU: O-(7-azobenzotriazole-1-yl)-N,N,N',N'-tetramethylurea tetrafluoroborate;
TBTU: O-(benzotriazole-1-yl)-N,N,N',N'-tetramethylurea tetrafluoroborate;
OMS: methanesulfonic acid ester;
OTS: p-toluenesulfonic acid ester.

The preparation of compounds of the present application is illustrated by but not limited to the following examples.

Compound 1a 4-methoxy-3-ethoxybenzaldehyde

To a 500 ml three-neck flask equipped with a mechanical stirrer and an inert gas tube were added 30.5 g of isovanillin, 55.2 g of potassium carbonate, 49.9 g of iodoethane and 140 ml of DMF. The mixture was stirred overnight at the room temperature. The mixture was poured into 1400 ml of water, and then the resultant mixture was extracted with ethyl acetate (600 ml×2). The ethyl acetate layers were combined. The organic phase was washed with saturated $Na_2CO_3$ (200 ml×3), 200 ml of water and 200 ml saturated NaCl, dried over anhydrous $MgSO_4$, and filtered. The solvent was evaporated to give a straw yellow solid. The solid was recrystallized with a mixed solvent of ethyl acetate and petroleum ether (1:4) to give a white needle crystal (32.9 g). MS (m/z): 181 $[M+1]^+$.

The following compounds 1b-1d were prepared with the same process as described above.

Compound 1b 4-ethoxy-3-methoxybenzaldehyde

The process for preparing the compound 1a was repeated with vanillin instead of isovanillin to obtain a solid product. MS (m/z): 181 $[M+1]^+$.

Compound 1c 3,4-dimethoxybenzaldehyde

The process for preparing the Example 1a was repeated with iodomethane instead of iodoethane to obtain a solid product. MS (m/z): 167 $[M+1]^+$.

Compound 1d 3-phenylmethoxy-4-methoxybenzaldehyde

The process for preparing the Example 1a was repeated with benzyl chloride instead of iodoethane to obtain a solid product. MS (m/z): 243 $[M+1]^+$.

Compound 2a 1-(3-ethoxy-4-methoxyphenyl)-2-(methylsulfonyl)-N-(trimethylsilyl)ethylamine To a 500 ml three-neck flask equipped with a magnetic stirrer and an inert gas tube were added 3.7 g of dimethyl sulfone and 160 ml of THF. The mixture was cooled to −78° C. and 22 ml of n-butyl lithium (2.2 M n-hexane solution) was added dropwise in the mixture. After the addition the mixture was maintained at −78° C. and stirred for 30 min to obtain A. In a 250 ml three-neck flask equipped with a magnetic stirrer and an inert gas tube was added 7.1 g of compound 1a. The flask was cooled in an ice-salt bath. 43 ml of lithium bis-(trimethylsilyl)amide (1.06 M THF solution) was added dropwise in the flask. After the addition the mixture was stirred for 15 min, and then 10 ml solution of boron trifluoride in diethyl ether was added dropwise to the mixture. The resultant mixture was stirred for 5 min to obtain B. B was transferred into A. The mixture was warmed slowly to the room temperature (over about 1.5 hours). The reaction was quenched with 200 ml of 1.6N $K_2CO_3$ solution. The mixture was stirred for 30 min and then separated. The aqueous layer was extracted with ethyl acetate (200 ml×3). All the organic layers were combined. The resulent organic phase was washed with 200 ml saturated NaCl, dried over anhydrous $MgSO_4$ and filtered. The solvent was evaporated to give 10 g of a straw yellow foam solid.

The following compounds 2b-2d were prepared with the same process as described above.

Compound 2b 1-(3-methoxy-4-ethoxyphenyl)-2-(methylsulfonyl)-N-(trimethylsilyl)ethylamine Compound 2c 1-(3,4-dimethoxyphenyl)-2-(methylsulfonyl)-N-(trimethylsilyl)ethylamine Compound 2d 1-(3-phenylmethoxy-methoxyphenyl)-2-(methylsulfonyl)-N-(trimethylsilyl)ethylamine Compound 3a 1-(3-ethoxy-4-methoxyphenyl)-2-(methylsulfonyl)ethylamine To a 500 ml of single-neck flask equipped with a magnetic stirrer were added 10 g of compound 2a, 100 ml of diethyl ether and 100 ml of 4N HCl. The mixture was stirred for 30 min at the room temperature and separated. The organic layer was extracted with 4N HCl (100 ml×3). The aqueous layers were combined. The pH of the aqueous phase was adjusted to 12 with 4N sodium hydroxide in an ice bath. The resultant mixture was extracted with ethyl acetate (200 ml×3). The organic layers were combined. The organic phase was washed with 200 ml of saturated NaCl, dried over anhydrous $MgSO_4$ and filtered. The solvent was evaporated. 1.5 g of a white solid was given after purified with column chromatography.

$^1$H NMR (CDCl$_3$): δ 6.93-6.84 (m, 3H), 4.60 (d, 1H, J=8 Hz), 4.12 (q, 2H, J=4 Hz), 3.87 (s, 3H), 3.37-3.21 (m, 2H), 2.92 (s, 3H), 1.86 (s, 2H), 1.48 (t, 3H, J=4 Hz); MS (m/z): 274 $[M+1]^+$; Chiral HPLC (isopropanol/n-hexane/diethylamine=35/65/0.1, Chiralcel® OJ-H column, 250×4.6 mm, 1.0 mL/min, @234 nm): 15.2 min (R-isomer, 49.8%), 17.3 min (S-isomer, 50.2%).

The following compounds 3b-3d were prepared with the same process as described above.

Compound 3b 1-(3-methoxy-4-ethoxyphenyl)-2-(methylsulfonyl)ethylamine MS (m/z): 274 [M+1]$^+$

Compound 3c 1-(3,4-dimethoxyphenyl)-2-(methylsulfonyl)ethylamine MS (m/z): 260 [M+1]$^+$

Compound 3d 1-(3-phenylmethoxy-methoxyphenyl)-2-(methylsulfonyl)ethylamine MS (m/z): 336 [M+1]$^+$

Compound 4a (S)-1-(3-ethoxy-4-methoxyphenyl)-2-(methylsulfonyl)ethylamine-N-acetyl-L-valine salt To a 100 ml of single-neck flask equipped with a magnetic stirrer, a reflux-condenser and an inert gas tube were added 6.920 g of compound 3a, 2.418 g of N-acetyl L-valine and 50 ml of anhydrous methanol. The mixture was refluxed in an oil-bath for 1 hour, stirred for 3 hours at the room temperature, and filtered in vacuo to give a white solid. The white solid was added in 25 ml of anhydrous methanol. The resultant mixture was refluxed for 1 hour, stirred at the room temperature for 3 hours, and filtered in vacuo to give 6.752 g of a white solid.

Compound 4b (S)-1-(3-ethoxy-4-methoxyphenyl)-2-(methylsulfonyl)-ethylamine

To a 250 ml of single-neck flask equipped with a magnetic stirrer were added 6.752 g of compound 4a, 150 ml of dichloromethane and 150 ml of water. To the mixture was added dropwise 5% sodium hydroxide aqueous solution in an ice bath to adjust pH to 11. The resultant mixture was separated. The aqueous layer was extracted with 150 ml of dichloromethane. The dichloromethane layers were combined. The organic phase was washed with 100 ml of saturated NaCl, dried over anhydrous MgSO$_4$, and filtered. The solvent was evaporated to give 2.855 g of a white solid (99.0% ee). MS (m/z): 274 [M+1]$^+$; Chiral HPLC (isopropanol/n-hexane/diethylamine=35/65/0.1, Chiralcel® OJ-H column, 250×4.6 mm, 1.0 mL/min, @234 nm): 15.2 min (R-isomer, 0.5%), 17.3 min (S-isomer, 99.5%).

Compound 4c (R)-1-(3-ethoxy-4-methoxyphenyl)-2-(methylsulfonyl)ethylamine-N-acetyl-D-leucine salt To a 100 ml of single-neck flask equipped with a magnetic stirrer, a reflux-condenser and an inert gas tube were added 1.365 g of compound 3a, 0.519 g of N-acetyl D-leucine, 10 ml of anhydrous methanol. The mixture was refluxed in an oil-bath for 1 hours, stirred for 3 hours at the room temperature, and filtered in vacuo to give 1.290 g of a white solid. The white solid was added in 10 ml of anhydrous methanol. The resultant mixture was refluxed for 1 hour, stirred for 3 hours at the room temperature, and filtered in vacuo to give 1.042 g of a white solid.

Compound 4d (R)-1-(3-ethoxy-4-methoxyphenyl)-2-(methylsulfonyl)ethylamine

To a 250 ml of single-neck flask equipped with a magnetic stirrer were added compound 4c, 50 ml of dichloromethane and 50 ml of water. To the mixture was added dropwise 5% sodium hydroxide aqueous solution in an ice bath to adjust pH to 11. The resultant mixture was separated. The aqueous layer was extracted with 50 ml of dichloromethane. The dichloromethane layers were combined. The organic phase was washed with 50 ml of saturated NaCl, dried over anhydrous MgSO$_4$, and filtered. The solvent was evaporated to give 0.622 g of a white solid (99.0% ee). MS (m/z): 274 [M+1]$^+$; Chiral HPLC (isopropyl alcohol/n-hexane/diethylamine=35/65/0.1, Chiralcel® OJ-H column, 250×4.6 mm, 1.0 mL/min, @234 nm): 15.2 min (R-isomer, 99.5%), 17.3 min (S-isomer, 0.5%).

Compound 5

3,4-dicyanothiophene

To a 2000 ml of three-neck flask equipped with a magnetic stirrer, a reflux-condenser and an inert gas tube were added 96.8 g of 3,4-dibrominethiophene, 104 g of cuprous cyanide and 100 ml of dried DMF. The mixture was heated at reflux for 4 hours and cooled to the room temperature. To the reaction mixture was added a solution of 400 g of FeCl$_3$.6H$_2$O in 700 ml of 1.7N hydrochloric acid. The reaction solution was maintained at 60° C.-70° C. for 30 min. 500 ml of DCM was added to the reaction solution after sufficiently cooled. The resultant mixture was divided into several portions. Each portion is 300 ml and extracted with DCM (300 ml×2). All DCM layers were combined. The extract was divided into several portions. Each portion is 600 ml and washed with 6N of hydrochloric acid (50 ml×2), water, saturated Na$_2$CO$_3$ aqueous solution and saturated saline solution sequentially, dried over anhydrous MgSO$_4$, and filtered. The solvent was evaporated to give a yellow solid. The yellow solid was washed with a mixed solvent of ethyl acetate and petroleum ether (1:1) and filtered to give 21 g of a white solid. NMR (CDCl$_3$): δ 8.07 (s, 2H).

Compound 6 thiophene-3,4-dicarboxylic acid

To a 500 ml of round-bottom flask equipped with an electromagnetic stirrer and a reflux-condenser were added 15.978 g of compound 5, 43.997 g of potassium hydroxide and 174 ml of ethylene glycol. The mixture was refluxed for 4 hours. After cooling, 350 ml of water was added to the reaction mixture. The resultant mixture was extracted with diethyl ether (100 ml×2). The diethyl ether layers were discarded. An excess amount of concentrated hydrochloric acid was added to the aqueous layer in an ice bath to give a white precipitate. The white precipitate was filtrated and the solid was dissolved in diethyl ether (about 2000 ml). The filtrate was extracted with diethyl ether (300 ml×3). All diethyl ether layers were combined. The organic phase was dried over anhydrous MgSO$_4$ and filtered. The solvent was evaporated to give 15 g of a white solid.

The white solid was recrystallized with water. $^1$H NMR (DMSO-d$_6$): δ 10.35 (brs, 2H), 8.17 (s, 2H); MS (m/z): 171 [M−1]$^+$.

Compound 7 thiophene[3,4-c]furan-1,3-diketone

To a 250 ml of round-bottom flask equipped with an electromagnetic stirrer, a reflux-condenser and a drying tube were added 15 g of compound 6 and 120 ml of acetic anhydride. The mixture was refluxed for 3 hours. The solvent was evaporated to give 13 g of a brown solid.

Compound 8

2-nitrothiophene-3,4-dicarboxylic acid

To a 250 ml of round-bottom flask equipped with an electromagnetic stirrer and a drying tube was added 40 ml of fuming nitric acid (content of 95%). The flask was cooled to 0° C.-5° C. with an ice bath. 10 g of compound 7 was added portionwise (1 g for each portion). After addition the mixture was reacted for 30 min at the current temperature (a yellow solid separated out). The reaction mixture was poured into 80 g of an ice-water mixture. The resultant mixture was extracted with ethyl acetate (100 ml×3). All ethyl acetate layers were combined. The organic phase was washed sequentially with 50 ml×2 of water and saturated saline solution, dried over anhydrous $MgSO_4$ and filtered. The solvent was evaporated to give 10 g of a yellow solid. MS (m/z): 216 $[M-1]^+$.

Compound 9

4-nitrothiophene[3,4-c]furan-1,3-diketone

To a 250 ml of round-bottom flask equipped with an electromagnetic stirrer, a reflux-condenser and a drying tube were added 10 g of compound 8 and 100 ml of acetic anhydride. The mixture was refluxed for 3 hours. The solvent was evaporated to give 9 g of a brown solid.

Example 1

5-(1-(3-ethoxy-4-methoxyphenyl)-2-(methylsulfonyl)ethyl)-1-nitro-5H-thiophene[3,4-c]pyrrole-4,6-diketone To a 250 ml of round-bottom flask equipped with an electromagnetic stirrer and a drying tube were added 1.99 g of compound 9, 2.73 g of compound 3a and 100 ml of THF. The mixture was stirred overnight at the room temperature. 1.944 g of CDI was added. The resultant mixture was refluxed in an oil-bath for 2 hours. The mixture was cooled to the room temperature in the open air. 200 ml of ethyl acetate and 150 ml of water were added. The mixture was extracted and separated. The organic layer was washed with 100 ml of 0.5N HCl, 100 ml of saturated NaCl, then dried over anhydrous $MgSO_4$ and filtered. The solvent was evaporated. 3.541 g of a light yellow solid was given after purified with column chromatography. MS (m/z): 453 $[M-1]^+$.

Example 2

5-(1-(3-ethoxy-4-methoxyphenyl)-2-(methylsulfonyl)ethyl)-1-amino-5H-thiophene[3,4-c]pyrrole-4,6-diketone To a 250 ml of round-bottom flask equipped with an electromagnetic stirrer, a reflux-condenser and a drying tube were added 2.27 g of 5-(1-(3-ethoxy-4-methoxyphenyl)-2-(methylsulfonyl)ethyl)-1-nitro-5H-thiophene[3,4-c]pyrrole-4,6-diketone and 100 ml of THF. The mixture was heated at reflux. 1.4 g of reductive powdery iron was added. The resultant mixture was refluxed for 2 hours and filtered in vacuo. The filtrate was evaporated. 200 ml of ethyl acetate and 150 ml of water was added. The mixture was extracted and separated. The organic layer was washed with 100 ml of water, 100 ml of saturated NaCl, then dried over anhydrous $MgSO_4$ and filtered. The solvent was evaporated. 1.68 g of a yellowish-brown solid was given after purified with column chromatography. MS (m/z): 425 $[M+1]^+$.

Example 3

N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide Method I: To a 50 ml of round-bottom flask equipped with an electromagnetic stirrer, a reflux-condenser and a drying tube were added 0.1 g of 5-(1-(3-ethoxy-4-methoxy phenyl)-2-(methylsulfonyl)ethyl)-1-amino-5H-thiophene[3,4-c]pyrrole-4,6-diketone, 0.005 g of DMAP and 10 ml of acetic anhydride. The mixture was heated to 60° C. and stirred for 6 hours. The solvent was evaporated. 0.02 g of a white solid was given after purified with column chromatography.

Method II: To a 50 ml of round-bottom flask equipped with an electromagnetic stirrer, a reflux-condenser and a drying tube were added 0.1 g of 5-(1-(3-ethoxy-4-methoxyphenyl)-2-(methylsulfonyl)ethyl)-1-amino-5H-thiophene[3,4-c]pyrrole-4,6-diketone and 5 ml of pyridine. 0.2 ml of acetylchloride was added dropwise in an ice bath and stirred for 1 hour at the room temperature. The solvent was evaporated. 50 ml of ethyl acetate and 20 ml of water were added. The mixture was extracted and separated. The organic layer was washed with 20 ml of 2N HCl, 20 ml of saturated NaCl, then dried over anhydrous $MgSO_4$ and filtered. The solvent was evaporated. 0.08 g of a white foamed solid was given after purified with column chromatography. MS (m/z): 465 $[M-1]^+$. $^1H$ NMR ($CDCl_3$): δ 9.12 (s, 1H), 7.33 (s, 1H), 7.08 (s, 1H), 7.07 (s, 1H), 6.83 (d, 1H, J=6 Hz), 5.82 (dd, 1H, J=3 Hz, J=7 Hz), 4.56 (dd, 1H, J=5 Hz, J=11 Hz), 4.12 (q, 2H, J=3 Hz), 3.86 (s, 3H), 3.76 (dd, 1H, J=5 Hz, J=11 Hz), 2.88 (s, 3H), 2.29 (s, 3H), 1.47 (t, 3H, J=5 Hz).

Example 4

5-(1-(3-ethoxy-4-methoxyphenyl)-2-(methylsulfonyl)ethyl)-5H-thiophene[3,4-c]pyrrole-4,6-diketone To a 50 ml of round-bottom flask equipped with an electromagnetic stirrer and a drying tube were added 0.077 g of compound 7, 0.137 g of compound 3a and 10 ml of THF. The mixture was stirred overnight at the room temperature. 0.122 g of CDI was added. The mixture was refluxed for 2 hours in an oil-bath and cooled to the room temperature in the open air. 100 ml of ethyl acetate and 50 ml of water was added in the mixture. The resultant mixture was extracted and separated. The organic layer was washed with 20 ml of 0.5N HCl, 20 ml of saturated NaCl, then dried over anhydrous $MgSO_4$ and filtered. The solvent was evaporated to give 0.121 g of a white solid. MS (m/z): 410 $[M+1]^+$.

Example 5

(S)-5-(1-(3-ethoxy-4-methoxyphenyl)-2-(methylsulfonyl)ethyl)-5H-thiophene[3,4-c]pyrrole-4,6-diketone The preparation procedure of Example 4 was repeated with compound 4b instead of compound 3a to give a solid product. MS (m/z): 410 [M+1]$^+$.

Example 6

(R)-5-(1-(3-ethoxy-4-methoxyphenyl)-2-(methylsulfonyl)ethyl)-5H-thiophene[3,4-c]pyrrole-4,6-diketone The preparation procedure of Example 4 was repeated with compound 4d instead of compound 3a to give a solid product. MS (m/z): 410 [M+1]$^+$.

Example 7

5-(1-(3-methoxy-4-ethoxyphenyl)-2-(methylsulfonyl)ethyl)-5H-thiophene[3,4-c]pyrrole-4,6-diketone The preparation procedure of Example 4 was repeated with compound 3b instead of compound 3a to give a solid product. MS (m/z): 410 [M+1]$^+$.

Example 8

5-(1-(3,4-dimethoxyphenyl)-2-(methylsulfonyl)ethyl)-5H-thiophene[3,4-c]pyrrole-4,6-diketone The preparation procedure of Example 4 was repeated with compound 3c instead of compound 3a to give a solid product. MS (m/z): 396 [M+1]$^+$.

Example 9

5-(1-(3-phenylmethoxy-4-methoxyphenyl)-2-(methylsulfonyl)ethyl)-5H-thiophene[3,4-c]pyrrole-4,6-diketone The preparation procedure of Example 4 was repeated with compound 3d instead of compound 3a to give a solid product. MS (m/z): 472 [M+1]$^+$.

Example 10

5-(1-(3-phenylmethoxy-4-methoxyphenyl)-2-(methylsulfonyl)ethyl)-1-nitro-5H-thiophene[3,4-c]pyrrole-4,6-diketone The preparation procedure of Example 1 was repeated with compound 3d instead of compound 3a to give a solid product. MS (m/z): 515 [M−1]$^+$.

Example 11

5-(1-(3-phenylmethoxy-4-methoxyphenyl)-2-(methylsulfonyl)ethyl)-1-amino-5H-thiophene[3,4-c]pyrrole-4,6-diketone The preparation procedure of Example 2 was repeated with the title compound of Example 10 instead of the title compound of Example 1 to give a solid product. MS (m/z): 487 [M+1]$^+$.

Example 12

N-(5-(1-(3-phenylmethoxy-4-methoxyphenyl)-2-(methylsulfonyl)ethyl)-4,6-dioxo-5,6-dihydro-4H-thiophene[3,4-e]pyrrole-1-yl)acetamide The preparation procedure of Example 3 was repeated with the title compound of Example 11 instead of the title compound of Example 2 to give a solid product. MS (m/z): 527 [M−1]$^+$.

Example 13

5-(1-(3,4-dimethoxyphenyl)-2-(methylsulfonyl)ethyl)-1-nitro-5H-thiophene[3,4-c]pyrrole-4,6-diketone The preparation procedure of Example 1 was repeated with compound 3c instead of compound 3a to give a solid product. MS (m/z): 439 [M−1]$^+$.

Example 14

5-(1-(3,4-dimethoxyphenyl)-2-(methylsulfonyl)ethyl)-1-amino-5H-thiophene[3,4-c]pyrrole-4,6-diketone The preparation procedure of Example 2 was repeated with the title compound of Example 13 instead of the title compound of Example 1 to give a solid product. MS (m/z): 411 [M+1]$^+$.

Example 15

5-(1-(3-methoxy-4-ethoxyphenyl)-2-(methylsulfonyl)ethyl)-1-nitro-5H-thiophene[3,4-c]pyrrole-4,6-diketone The preparation procedure of Example 1 was repeated with compound 3b instead of compound 3a to give a solid product. MS (m/z): 453 [M−1]$^+$.

Example 16

5-(1-(3-methoxy-4-ethoxyphenyl)-2-(methylsulfonyl)ethyl)-1-amino-5H-thiophene[3,4-c]pyrrole-4,6-diketone The preparation procedure of Example 2 was repeated with the title compound of Example 15 instead of the title compound of Example 1 to give a solid product. MS (m/z): 425 [M+1]$^+$.

Example 17

5-(1-(3-ethoxy-4-methoxyphenyl)-2-(methylsulfonyl)ethyl)-1-methylamino-5H-thiophene[3,4-c]pyrrole-4,6-diketone In 10 ml of acetone was dissolved 0.085 g of the title compound of Example 2. To the mixture was added 0.5 ml of iodomethane. The resultant mixture was heated to 80° C. and reacted for 6 hours. After cooling, 100 ml of water was added. The mixture was extracted with ethyl acetate (30 ml×3). The organic layers were combined. The organic phase was washed with 30 ml of water and saturated saline aqueous solution sequentially, dried over anhydrous MgSO$_4$ and fil-

Example 18

2-chloro-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide The preparation procedure of Method II of Example 3 was repeated with compound chloroacetylchloride instead of compound acetylchloride to give a solid product. MS (m/z): 499 [M−1]$^+$.

Example 19

N-(5-(1-(3-ethoxy-4-methoxyphenyl)-2-(methylsulfonyl)ethyl)-4,6-diketone-5,6-dihydro-4H-thiophene[3,4-c]pyrrole-1-yl)methanesulfonamide The preparation procedure of Method II of Example 3 was repeated with compound methanesulfonyl chloride instead of compound acetylchloride to give a solid product. MS (m/z): 501 [M−1]$^+$.

Example 20

(S)-1-nitro-5-(1-(3-ethoxy-4-methoxyphenyl)-2-(methylsulfonyl)ethyl)-5H-thiophene[3,4-c]pyrrole-4,6-diketone The preparation process of Example 1 was repeated with compound 4b and compound 9.

Example 21

(S)-1-amino-5-(1-(3-ethoxy-4-methoxyphenyl)-2-(methylsulfonyl)ethyl)-5H-thiophene[3,4-c]pyrrole-4,6-diketone The preparation process of Example 2 was repeated with the title compound of Example 20. MS (m/z): 425 [M+1]$^+$.

Example 22

(R)-1-nitro-5-(1-(3-ethoxy-4-methoxyphenyl)-2-(methylsulfonyl)ethyl)-5H-thiophene[3,4-c]pyrrole-4,6-diketone The preparation process of Example 1 was repeated with compound 4d and compound 9.

Example 23

(R)-1-amino-5-(1-(3-ethoxy-4-methoxyphenyl)-2-(methylsulfonyl)ethyl)-5H-thiophene[3,4-c]pyrrole-4,6-diketone The preparation process of Example 2 was repeated with the title compound of Example 22. MS (m/z): 425 [M+1]$^+$.

Example 24

(S)—N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide The preparation process of Example 3 was repeated with the title compound obtained from Example 21. MS (m/z): 465 [M−1]$^+$; Chiral HPLC (anhydrous ethanol/n-hexane/diethylamine=40/60/0.1, Chiralcel® OJ-H column, 250×4.6 mm, 1.0 mL/min, @230 nm): 9.8 min (R-isomer, 1.2%), 13.8 min (S-isomer, 98.8%). $^1$H NMR (CDCl$_3$): δ 9.27 (s, 1H), 7.30 (s, 1H), 7.07 (s, 1H), 7.05 (s, 1H), 6.81 (d, 1H, J=6 Hz), 5.81 (dd, 1H, J=3 Hz, J=7 Hz), 4.54 (dd, 1H, J=8 Hz, J=11 Hz), 4.08 (q, 2H, J=3 Hz), 3.84 (s, 3H), 3.73 (dd, 1H, J=8 Hz, J=11 Hz), 2.86 (s, 3H), 2.27 (s, 3H), 1.45 (t, 3H, J=5 Hz).

Example 25

(R)—N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide The preparation process of Example 3 was repeated with the title compound given in Example 23. 465 [M−1]$^+$; Chiral HPLC (anhydrous ethanol/n-hexane/diethylamine=40/60/0.1, Chiralcel® OJ-H column, 250×4.6 mm, 1.0 mL/min, @230 nm): 9.8 min (R-isomer, 99.5%), 13.8 min (S-isomer, 0.5%).

Example 26

N-(5-(1-(3-methoxy-4-ethoxyphenyl)-2-(methylsulfonyl)ethyl)-4,6-dioxo-5,6-dihydro-4H-thiophene[3,4-c]pyrrole-1-yl)acetamide The process for preparing the title compound of Example 3 was repeated with the title compound of Example 16. MS (m/z): 465 [M−1]$^+$.

Example 27

N-(5-(1-(3-phenylmethoxy-4-methoxyphenyl)-2-(methylsulfonyl)ethyl)-4,6-dioxo-5,6-dihydro-4H-thiophene[3,4-c]pyrrole-1-yl)propionamide The preparation procedure of Example 3 was repeated with the title compound of Example 11 and propionyl chloride to give a solid product. MS (m/z): 541 [M−1]$^+$.

Example 28

2-(dimethylamino)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide In 10 ml of tetrahydrofuran was dissolved 50 mg of the title compound of Example 18. 0.3 ml solution of 2N dimethylamine in tetrahydrofuran was added. The mixture was stirred overnight at the room temperature. After the reaction completed, 100 ml of water was added. The resultant mixture was extracted with ethyl acetate (40 ml×3). The organic layers were combined. The organic phase was washed with 40 ml of water and saturated saline aqueous solution sequentially, dried over anhydrous magnesium sulfate, filtered. The solvent was evaporated. 40 mg of a solid was given after separation with silica gel column chromatography. MS (m/z): 510 [M+1]$^+$.

Example 29

2-(diethylamino)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide The preparation process in Example 28 was repeated with diethylamine instead of dimethylamine to give the title compound of Example 29, MS (m/z): 538 [M+1]$^+$.

Example 30

2-(piperidyl)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide The preparation process in Example 28 was repeated with piperidine instead of dimethylamine to give the title compound of Example 30, MS (m/z): 550 [M+1]$^+$.

Example 31

2-(morpholinyl)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide The preparation process in Example 28 was repeated with morpholine instead of dimethylamine to give the title compound of Example 31, MS (m/z): 552 [M+1]$^+$.

Example 32

Pharmacological Research

1. Effects of Mononuclear Cells (PBMCs) Stimulated by LPS on TNFα

The research in respect of cytokine TNFα release by PBMCs in the human peripheral blood after stimulated by lipopolysaccharide (LPS) can be carried out in vitro. The research method for inhibiting cytokine TNFα release by PBMCs upon stimulation by LPS with the pharmaceutical active ingredients in the present application is described as follows.

PBMCs are obtained from heparin treated blood of at least three volunteer donors. The heparin treated blood of at least three volunteer donors was subject to gradient separation of the known method to obtain PBMCs. The PBMCs were collected and washed with 1640 medium (10% fetal bovine serum, 2 mM L-glutamine, 100 mM mercaptoethanol, 50 µg/ml streptomycin and 50 U/ml penicillin) three times. The PBMCs was added into a 24-well plate and prepared with a concentration of 1×10$^6$ cell/ml with 1640 medium. A compound to be tested was dissolved in dimethylsulfoxide and prepared as a solution of the compound to be tested with a required concentration. The solution was added into the cell cultures. After incubated in a CO$_2$ incubator (5% CO$_2$, 90% humidity) for 1 hour, LPS (Sigma) was added until 0.1 µg/ml (except for the control).

After the medium was further incubated for 20 hours, the content of TNFα in the supernate of the PBMCs medium was measured by the standard method with commercial ELISA kit (U.S Genzyme Co). The inhibition ratio of TNFα was calculated by the measured value of control well without treated by active ingredients and the measured value of the test well using the test compound. The concentration of generating 50% inhibition of the TNFα release (IC$_{50}$ value) was calculated with nonlinear regression analysis. Each concentration was measured twice simultaneously and an average value was calculated. Some results of the test are shown in Table 1.

TABLE 1

Activity on Inhibition of TNFα Release by Mononuclear Cells Stimulated by LPS

| Compounds | IC$_{50}$ (µm) | Compounds | IC$_{50}$ (µm) | Compounds | IC$_{50}$ (µm) |
|---|---|---|---|---|---|
| Example 24 | 0.065 | Example 6 | 2.5 | Example 11 | >10 |
| Example 25 | 1.19 | Example 2 | 0.524 | Example 12 | >10 |
| Example 3 | 0.296 | Example 21 | 0.142 | Example 26 | >10 |
| Example 4 | 0.886 | Example 23 | 1.9 | Example 18 | 0.216 |
| Example 5 | 0.376 | Example 9 | 7.5 | Example 19 | 0.288 |

2. Inhibitory Activity and Selective Inhibitory Activity of Compounds on PDE Enzymes (1) The inhibitory actions of compounds on activity of hydrolyzing cAMP with PDE4 enzyme were assayed by the inhibitory activity of PDE4 enzyme. The procedures are described as follows.

Humanized PDE4A1A, PDE4B1 and PDE4D2 were purchased from BPS bioscience (catalogue Nos.: 60040, 60041 and 60043, respectively). The enzyme reactions were carried out in 10 mM Tris-HCl (pH 7.4) and 1 mM MgCl$_2$. The concentration of cAMP was 5 µM. The reaction was maintained at 37° C. for 15 min to 30 min so that the consumption of the substrate was controlled within 20%. The reaction was quenched with equal volume of acetonitrile. The production amount of the substrate AMP was measured by HPLC-MS. The inhibitory activity of compounds on PDE4 enzyme was obtained by comparing the production amounts of the AMP in the experimental groups having the compounds with those of the control groups having no compounds. Data are shown in Table 2.

(2) Inhibitory Activity of PDE2 (Selectivity of PDE Enzyme):

Humanized PDE2A was purchased from BPS bioscience (catalogue No.: 60020). The enzyme reaction was carried out in 10 mM Tris-HCl (pH 7.4) and 1 mM MgCl$_2$. The concentration of cAMP was 5 µM, The reaction was maintained at 37° C. for 30 min so that the consumption of the substrate was controlled within 20%. The reaction was quenched with equal volume of acetonitrile. The production amount of the substrate AMP was measured by HPLC-MS. The inhibitory activity of compounds on PDE2 was obtained by comparing the production amounts of the AMP in the experimental groups having the compounds with those of the control groups having no compounds. Data are shown in Table 2.

TABLE 2

Inhibitory Activity of PDE4 Enzyme and Selective Inhibitory Activity of PDE Enzymes

| Compounds | PDE4B1 IC$_{50}$ (µm) | PDE4D2 IC$_{50}$ (µm) | PDE4A1A IC$_{50}$ (µm) | PDE2A IC$_{50}$ (µm) |
|---|---|---|---|---|
| Example 24 | 0.178 | 0.114 | 0.104 | >50 |
| Example 3 | 0.256 | 0.224 | 0.208 | 36 |
| Example 4 | 1.2 | 0.329 | 0.366 | |
| Example 5 | 0.368 | | | |
| Example 6 | 2.3 | 0.315 | | |
| Example 2 | 0.212 | 1.9 | | |
| Example 20 | 0.026 | | | |
| Example 23 | 0.718 | 0.055 | | |
| Example 9 | 5.3 | 0.831 | | |
| Example 11 | 1.0 | | | |

TABLE 2-continued

Inhibitory Activity of PDE4 Enzyme and Selective
Inhibitory Activity of PDE Enzymes

| Compounds | PDE4B1 IC$_{50}$ (μm) | PDE4D2 IC$_{50}$ (μm) | PDE4A1A IC$_{50}$ (μm) | PDE2A IC$_{50}$ (μm) |
|---|---|---|---|---|
| Example 12 | 1.2 | | | |
| Example 18 | 0.618 | | | |
| Example 19 | 0.167 | | | |

From the foregoing it will be appreciated that, although specific embodiments of the present application have been described herein for purposes of illustration, various modifications may be made without deviating from the spirit and scope of the present application. Accordingly, the present application is not limited except as by the appended claims.

What is claimed is:

1. A compound of formula (I), a stereoisomer, an enantiomer or a tautomer, or a mixture of stereoisomer thereof, a pharmaceutically acceptable salt thereof, a polymorph thereof, a solvate thereof, or a prodrug thereof:

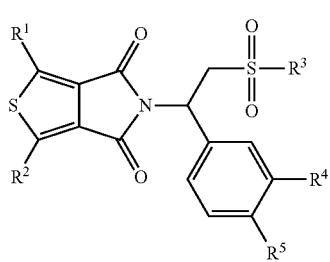

Formula (I)

wherein,
$R^1$ and $R^2$ are each independently selected from the group consisting of hydrogen, halogen, optionally substituted alkyl, optionally substituted alkoxy, hydroxy, cyano, nitro and optionally substituted $NR^6R^7$;
$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;
$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;
$R^6$ and $R^7$ are each independently selected from the group consisting of hydrogen, optionally substituted alkyl, optionally substituted aryl, optionally substituted C(O)$R^8$ and optionally substituted SO$_2$R$^8$, or $R^6$ and $R^7$ together represent optionally substituted 1,4-butylidene, optionally substituted 1,5-pentylidene, optionally substituted 1,6-hexylidene or optionally substituted CH$_2$CH$_2$XCH$_2$CH$_2$, wherein X is selected from the group consisting of O, S and NR$^8$; and
$R^8$ is selected from the group consisting of hydrogen and optionally substituted alkyl.

2. A compound of claim 1, wherein $R^1$ and $R^2$ are each independently selected from the group consisting of hydrogen, methyl, ethyl, nitro, NH$_2$, NHCH$_3$, CH$_3$C(O)NH, CH$_3$CH$_2$C(O)NH, CH$_3$SO$_2$NH and ClCH$_2$C(O)NH.

3. A compound of claim 1, wherein $R^3$ is C$_1$-C$_8$ alkyl.

4. A compound of claim 1, wherein $R^4$ and $R^5$ are each independently selected from the group consisting of C$_1$-C$_8$ alkoxy, halogen substituted C$_1$-C$_8$ alkoxy and C$_5$-C$_{12}$ aryloxy.

5. A compound of claim 1, wherein $R^8$ is selected from the group consisting of hydrogen, C$_1$-C$_8$ alkyl, halogen substituted C$_1$-C$_8$ alkyl, (C$_1$-C$_8$ alkyl substituted amino) substituted C$_1$-C$_8$ alkyl and C$_3$-C$_{12}$ heterocycloalkyl substituted C$_1$-C$_8$ alkyl.

6. A compound of claim 1, which is selected from the group consisting of:
N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide,
1-amino-5-(1-(3-ethoxy-4-methoxyphenyl)-2-(methylsulfonyl)ethyl)-5H-thiophene[3,4-c]pyrrole-4,6-diketone,
(S)—N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide,
(R)—N-(5-(1-(3-ethoxy-4-methoxyphenyl)-2-(methylsulfonyl)ethyl)-4,6-dioxo-5,6-dihydro-4H-thiophene[3,4-c]pyrrole-1-yl)acetamide,
5-(1-(3-ethoxy-4-methoxyphenyl)-2-(methylsulfonyl)ethyl)-1-nitro-5H-thiophene[3,4-c]pyrrole-4,6-diketone,
N-(5-(1-(3-methoxy-4-ethoxyphenyl)-2-(methylsulfonyl)ethyl)-4,6-dioxo-5,6-dihydro-4H-thiophene[3,4-c]pyrrole-1-yl)acetamide,
N-(5-(1-(3,4-dimethoxyphenyl)-2-(methylsulfonyl)ethyl)-4,6-dioxo-5,6-dihydro-4H-thiophene[3,4-c]pyrrole-1-yl)acetamide,
5-(1-(3-ethoxy-4-methoxyphenyl)-2-(methylsulfonyl)ethyl)-5H-thiophene[3,4-c]pyrrole-4,6-diketone,
(S)-5-(1-(3-ethoxy-4-methoxyphenyl)-2-(methylsulfonyl)ethyl)-5H-thiophene[3,4-c]pyrrole-4,6-diketone,
(R)-5-(1-(3-ethoxy-4-methoxyphenyl)-2-(methylsulfonyl)ethyl)-5H-thiophene[3,4-c]pyrrole-4,6-diketone,
(S)-5-(1-(3-methoxy-4-ethoxyphenyl)-2-(methylsulfonyl)ethyl)-5H-thiophene[3,4-c]pyrrole-4,6-diketone,
(S)-5-(1-(3,4-dimethoxyphenyl)-2-(methylsulfonyl)ethyl)-5H-thiophene[3,4-c]pyrrole-4,6-diketone,
5-(1-(3-phenylmethoxy-4-methoxyphenyl)-2-(methylsulfonyl)ethyl)-5H-thiophene[3,4-c]pyrrole-4,6-diketone,
5-(1-(3-phenylmethoxy-4-methoxyphenyl)-2-(methylsulfonyl)ethyl)-1-nitro-5H-thiophene[3,4-c]pyrrole-4,6-diketone,
5-(1-(3-phenylmethoxy-4-methoxyphenyl)-2-(methylsulfonyl)ethyl)-1-amino-5H-thiophene[3,4-c]pyrrole-4,6-diketone,
N-(5-(1-(3-phenylmethoxy-4-methoxyphenyl)-2-(methylsulfonyl)ethyl)-4,6-dioxo-5,6-dihydro-4H-thiophene[3,4-c]pyrrole-1-yl)acetamide,
5-(1-(3,4-dimethoxyphenyl)-2-(methylsulfonyl)ethyl)-1-nitro-5H-thiophene[3,4-c]pyrrole-4,6-diketone,
5-(1-(3,4-dimethoxyphenyl)-2-(methylsulfonyl)ethyl)-1-amino-5H-thiophene[3,4-c]pyrrole-4,6-diketone,
5-(1-(3-methoxy-4-ethoxyphenyl)-2-(methylsulfonyl)ethyl)-1-nitro-5H-thiophene[3,4-c]pyrrole-4,6-diketone,
5-(1-(3-methoxy-4-ethoxyphenyl)-2-(methylsulfonyl)ethyl)-1-amino-5H-thiophene[3,4-c]pyrrole-4,6-diketone, 5-(1-(3-ethoxy-4-methoxyphenyl)-2-(methylsulfonyl)ethyl)-1-methylamino-5H-thiophene[3,4-c]pyrrole-4,6-diketone,
2-chloro-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide,
N-(5-(1-(3-ethoxy-4-methoxyphenyl)-2-(methylsulfonyl)ethyl)-4,6-diketone-5,6-dihydro-4H-thiophene[3,4-c]pyrrole-1-yl)methanesulfonamide,
(S)-1-amino-5-(1-(3-ethoxy-4-methoxyphenyl)-2-(methylsulfonyl)ethyl)-5H-thiophene[3,4-c]pyrrole-4,6-diketone,
(R)-1-amino-5-(1-(3-ethoxy-4-methoxyphenyl)-2-(methylsulfonyl)ethyl)-5H-thiophene[3,4-c]pyrrole-4,6-diketone,
N-(5-(1-(3-ethoxy-4-difluoromethoxyphenyl)-2-(methylsulfonyl)ethyl)-4,6-dioxo-5,6-dihydro-4H-thiophene[3,4-c]pyrrole-1-yl)acetamide,
N-(5-(1-(3-ethoxy-4-trifluoromethoxyphenyl)-2-(methylsulfonyl)ethyl)-4,6-dioxo-5,6-dihydro-4H-thiophene[3,4-c]pyrrole-1-yl)acetamide,
(S)—N-(5-(1-(3-ethoxy-4-difluoromethoxyphenyl)-2-(methylsulfonyl)ethyl)-4,6-dioxo-5,6-dihydro-4H-thiophene[3,4-c]pyrrole-1-yl)acetamide,
(R)—N-(5-(1-(3-ethoxy-4-difluoromethoxyphenyl)-2-(methylsulfonyl)ethyl)-4,6-dioxo-5,6-dihydro-4H-thiophene[3,4-c]pyrrole-1-yl)acetamide,
(S)—N-(5-(1-(3-ethoxy-4-trifluoromethoxyphenyl)-2-(methylsulfonyl)ethyl)-4,6-dioxo-5,6-dihydro-4H-thiophene[3,4-c]pyrrole-1-yl)acetamide,
(R)—N-(5-(1-(3-ethoxy-4-trifluoromethoxyphenyl)-2-(methylsulfonyl)ethyl)-4,6-dioxo-5,6-dihydro-4H-thiophene[3,4-c]pyrrole-1-yl)acetamide,
N-(5-(1-(3-phenylmethoxy-4-methoxyphenyl)-2-(methylsulfonyl)ethyl)-4,6-dioxo-5,6-dihydro-4H-thiophene[3,4-c]pyrrole-1-yl)propionamide,
2-(dimethylamino)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide,
2-(diethylamino)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide,
2-(piperidyl)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide, and
2-(morpholinyl)-N-(5-(1-(3-ethoxy-4-methoxyphenyl)-2-(methylsulfonyl)ethyl)-4,6-diketone-5,6-dihydro-4H-thiophene[3,4-c]pyrrole-1-yl)acetamide.

7. A process for preparing a compound of formula (I), comprising reacting a compound of formula (A-IV) with a compound of formula (A-VII) to obtain the compound of formula (I):

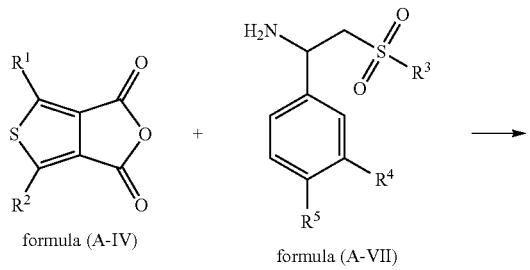

formula (A-IV)  formula (A-VII)

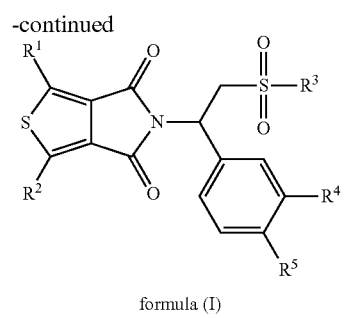

formula (I)

wherein,
$R^1$ and $R^2$ are each independently selected from the group consisting of hydrogen, halogen, optionally substituted alkyl, optionally substituted alkoxy, hydroxy, cyano, nitro and optionally substituted $NR^6R^7$;
$R^3$ is selected from the group consisting of hydroxy, optionally substituted alkyl, optionally substituted alkoxy, optionally substituted alkyl(alkylene)oxy, optionally substituted aryl, optionally substituted aryl(alkylene)oxy and optionally substituted $NR^6R^7$;
$R^4$ and $R^5$ are each independently selected from the group consisting of hydrogen, hydroxy, optionally substituted alkyl, optionally substituted alkoxy, optionally substituted alkylthio, cyano, optionally substituted cycloalkyl, optionally substituted (alkylene)cycloalkyl, optionally substituted cycloalkyl(alkylene)oxy, optionally substituted cycloalkyloxy, optionally substituted aryl, optionally substituted aryloxy and optionally substituted aryl(alkylene)oxy;
$R^6$ and $R^7$ are each independently selected from the group consisting of hydrogen, optionally substituted alkyl, optionally substituted aryl, optionally substituted $C(O)R^8$ and optionally substituted $SO_2R^8$, or $R^6$ and $R^7$ together represent optionally substituted 1,4-butylidene, optionally substituted 1,5-pentylidene, optionally substituted 1,6-hexylidene or optionally substituted $CH_2CH_2XCH_2CH_2$, wherein X is selected from the group consisting of O, S and $NR^8$;
$R^8$ is selected from the group consisting of hydrogen and optionally substituted alkyl.

8. A process of claim 7, wherein a tertiary amine is added as a catalyst in reacting a compound of formula (A-IV) with a compound of formula (A-VII) to obtain the compound of formula (I).

9. A pharmaceutical composition comprising a pharmaceutically acceptable carrier and an effective amount of a compound of claim 1.

10. A pharmaceutical composition of claim 9 further comprising at least another active ingredient.

11. A pharmaceutical composition of claim 10, wherein the active ingredient is selected from the group consisting of nitrogen mustard, aziridine, methyl melamine, alkyl sulphonate, nitrosourea, triazene, folacin, pyrimidine analogue, purine analogue, vinca alkaloid, epipodophyllotoxin, antibiotic, topoisomerase inhibitor, anticancer vaccine, acivicin, aclarubicin, acodazole hydrochloride, acronine, adozelesin, aldesleukin, ambomycin, ametantrone acetate, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin hydrochloride, droloxifene, epirubicin hydrochloride, esorubicin hydrochloride, estramustine, etanidazole, etoposide, floxuridine, fluorouracil, fluorocitabine, gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, angiogenesis inhibitor, camptothecin, hexadecadrol, aspirin, acetaminophen, indometacin, ibuprofen, ketoprofen, meloxicam, corticosteroid and adrenal corticosteroid.

12. A pharmaceutical composition of claim 9 formulated as tablet, solution, granule, patch, ointment, capsule, aerosol or suppository administered via parenteral, transdermal, mucosa, nasal, buccal, sublingual or oral route.

13. A method for reducing activity of PDE4 enzyme in vitro, comprising contacting PDE4 enzyme with an effective amount of a compound of claim 1.

14. A method for treating a disease or condition mediated by PDE4 enzyme, comprising administering to a subject in need thereof a therapeutically effective amount of a compound of claim 1, wherein the disease or condition is selected from the group consisting of microorganism infection, microorganism infective syndrome, asthma, chronic obstructive pulmonary disease (COPD), allergic rhinitis, allergic dermatitis, arthritis, and ichorrhemia.

15. A method of claim 14, wherein the subject in need thereof is administered a unit dose of 0.1 mg-1000 mg of the compound.

16. A method of claim 14, wherein when administering to the subject in need thereof an effective amount of the compound, the method further comprises administering to the subject in need thereof at least another active ingredient.

17. A method of claim 16, wherein the active ingredient is selected from the group consisting of nitrogen mustard, aziridine, methylmelamine, alkyl sulphonate, nitrosourea, triazene, folacin, pyrimidine analogue, purine analogue, vinca alkaloid, epipodophyllotoxin, antibiotic, topoisomerase inhibitor, anticancer vaccine, acivicin, aclarubicin, hydrochloride acodazole, acronine, adozelesin, aldesleukin, ambomycin, acetate ametantrone, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin hydrochloride, droloxifene, epirubicin hydrochloride, esorubicin hydrochloride, estramustine, etanidazole, etoposide, floxuridine, fluorouracil, fluorocitabine, gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, angiogenesis inhibitor, camptothecin, hexadecadrol, aspirin, acetaminophen, indometacin, ibuprofen, ketoprofen, meloxicam, corticosteroid and adrenal corticosteroid.

18. A method of claim 17, wherein the subject in need thereof is simultaneously, concurrently, separately or sequentially administered the compound and at least another active ingredient.

19. A compound of claim 1, wherein $R^3$ is selected from the group consisting of methyl, ethyl and propyl.

20. A compound of claim 1, wherein $R^4$ and $R^5$ are each independently selected from the group consisting of methoxy, difluoromethoxy, trifluoromethoxy, ethoxy, propoxy and benzyloxy.

21. A compound of claim 1, wherein $R^8$ is selected from the group consisting of hydrogen, methyl, ethyl, dimethylaminomethyl, diethylaminomethyl, piperidylmethyl and morpholinylmethyl.

22. A process of claim 8, wherein the tertiary amine is selected from the group consisting of pyridine, 4-dimethylaminopyridine, 4-pyrrolidinylpyridine and a mixture thereof.

* * * * *